US012577277B2

(12) United States Patent
Jungnelius et al.

(10) Patent No.: US 12,577,277 B2
(45) Date of Patent: Mar. 17, 2026

(54) METHOD FOR SEPARATING BIOMOLECULES

(71) Applicant: CYTIVA SWEDEN AB, Uppsala (SE)

(72) Inventors: Niklas Jungnelius, Uppsala (SE);
Andreas Castan, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 1067 days.

(21) Appl. No.: 17/616,577

(22) PCT Filed: Jun. 11, 2020

(86) PCT No.: PCT/EP2020/066173
§ 371 (c)(1),
(2) Date: Dec. 3, 2021

(87) PCT Pub. No.: WO2020/254176
PCT Pub. Date: Dec. 24, 2020

(65) Prior Publication Data
US 2022/0242903 A1 Aug. 4, 2022

(30) Foreign Application Priority Data

Jun. 17, 2019 (GB) ..................................... 1908612

(51) Int. Cl.
*B01D 15/18* (2006.01)
*B01D 15/20* (2006.01)
(Continued)

(52) U.S. Cl.
CPC ............ *C07K 1/36* (2013.01); *B01D 15/1871* (2013.01); *B01D 15/203* (2013.01);
(Continued)

(58) Field of Classification Search
CPC ........ C07K 1/36; C07K 1/22; B01D 15/1871; B01D 15/203; B01D 15/424; C12M 23/14; C12M 29/10; C12M 41/26; C12M 47/10
See application file for complete search history.

(56) References Cited

U.S. PATENT DOCUMENTS

2014/0255994 A1 9/2014 Konstantinov et al.
2015/0353896 A1 12/2015 Bruninghaus et al.
(Continued)

FOREIGN PATENT DOCUMENTS

CN 103562145 A 2/2014
CN 104640973 A 5/2015
(Continued)

OTHER PUBLICATIONS

Steinebach, F., "Continuous counter-current chromatography for capture and polishing steps in biopharmaceutical production", Biotechnology Journal, 11, pp. 1126-1141. (Year: 2016).*
(Continued)

*Primary Examiner* — Benjamin L Lebron
(74) *Attorney, Agent, or Firm* — Eversheds-Sutherland (US) LLP

(57) ABSTRACT

The present disclosure is directed to method (100) for separating a biomolecule from a fluid (2), wherein the biomolecule is produced by biological cells in a perfusion bioreactor (3), the method comprising: forwarding (110) a product fluid comprising the biomolecule and biological cells from the perfusion bioreactor (3) during a bioreactor product output time period; loading (210) a first separation device (4) with the product fluid obtained in step (110) during a first separation loading time period, which constitutes a first part of a first separation cycle time period; pausing (130) the forwarding of the product fluid from the perfusion bioreactor during a bioreactor non-product output (Continued)

time period; and pausing (220) the loading of the first separation device (4) during a second part of the first separation cycle time period. Also disclosed are a computer-implemented method performed by a controller configured to control a separation of a biomolecule from a fluid (2), and further a controller, a computer program, and a computer program product.

20 Claims, 12 Drawing Sheets

(51) Int. Cl.

| | | |
|---|---|---|
| *B01D 15/42* | (2006.01) | |
| *C07K 1/22* | (2006.01) | |
| *C07K 1/36* | (2006.01) | |
| *C12M 1/00* | (2006.01) | |
| *C12M 1/34* | (2006.01) | |

(52) U.S. Cl.
CPC .............. *B01D 15/424* (2013.01); *C07K 1/22* (2013.01); *C12M 23/14* (2013.01); *C12M 29/10* (2013.01); *C12M 41/26* (2013.01); *C12M 47/10* (2013.01)

(56) References Cited

U.S. PATENT DOCUMENTS

| | | | |
|---|---|---|---|
| 2017/0204446 | A1 | 7/2017 | Cattaneo |
| 2018/0117495 | A1 | 5/2018 | Schwan et al. |
| 2018/0298323 | A1 | 10/2018 | Lipkens et al. |

FOREIGN PATENT DOCUMENTS

| | | | |
|---|---|---|---|
| CN | 105263952 A | 1/2016 | |
| CN | 105377874 A | 3/2016 | |
| CN | 106661083 A | 5/2017 | |
| CN | 107683285 A | 2/2018 | |
| CN | 108424851 A | 8/2018 | |
| WO | 20110130617 A2 | 10/2011 | |
| WO | 20140145065 A1 | 9/2014 | |
| WO | 20180187789 A1 | 10/2018 | |

OTHER PUBLICATIONS

Jungnelius, N., and M. Bisshops, "Process intensification—so much more than continuous bioprocessing", Engineering Conferences International, Integrated Continuous Biomanufacturing V. Oct. 9-13, 2022.*
F. Steinebach et al., "Continuous counter-current chromatography for capture and polishing steps in biopharmaceutical production" Biotechnol. J. 2016, 11, pp. 1126-1141.
R. Godawat et al. "End-to-end integrated fully continuous production of recombinant monoclonal antibodies" Journal of Biotechnology, (2015) 8 pages.
D.J. Karst et al. "Process Performance and Product Quality in an Integrated Continuous Antibody Production Process" Biotechnology and Bioengineering, vol. 14 No. 2, Feb. 2, 2017.
M. Morbidelli, "End-to-end integrated Continuous Manufacture of Therapeutic Proteins" Cell Culture & Downstream World Congress, (Feb. 2017).
PCT, "International Search Report & Written Opinion" App. No. PCT/EP2020/066173, mailed Sep. 22, 2020, 108 pages.
IPO, "Search and Examination Report" App. No. GB 1908612.3, mailed Nov. 26, 2019, 3 pages.
Chinese Office Action and Search Report for corresponding CN Application No. 202080044107.X, mailed Oct. 31, 2023, 11 pages.
Feng, Lei; Establishment of an industrial-scale PRRSV proliferation process in a bioreactor, Jiangsu Agricultural Science, vol. 44 No. 2, pp. 247-251, 2016.

* cited by examiner

600

605 Generating a model

610 Obtaining measurement results

620 Generating control parameters based on the measurement results and a model

630 Controlling separation of a biomolecule using the generated control parameters

210 Measurement result obtainer

220 Bioprocess controller

230 Parameter generator

240 Model generator

METHOD FOR SEPARATING BIOMOLECULES

CROSS REFERENCE TO RELATED APPLICATIONS

This application is a U.S. National Phase Application of PCT/EP2020/066173, filed on Jun. 11, 2020, which claims the benefit of GB Application No. 1908612.3, filed on Jun. 17, 2019, the entire contents of which are incorporated by reference herein.

FIELD OF THE DISCLOSURE

The present disclosure relates to the field of separation of biomolecules, and in particular is directed to a method for separating biomolecules from a fluid, more particularly wherein the biomolecules are produced by biological cells in a perfusion bioreactor. Further disclosed is a computer-implemented method performed by a controller configured to control a method for separating biomolecules from a fluid, as well as a controller operative to perform any of the steps of the disclosed methods, a computer program and a computer program product.

BACKGROUND OF THE DISCLOSURE

Production of biomolecules in biological host cells by use of perfusion bioreactors is known in the art. The major advantage of the perfusion mode is high cell number and high productivity in a relatively small-size bioreactor as compared with batch/fed-batch. Characteristics of a perfusion process for producing target biomolecules in cells include that media is fed continuously to the bioreactor and harvest is removed continuously from the bioreactor while the cells are retained inside the bioreactor. The bioreactor has two output channels, a first one for removing excess cells from the bioreactor by so-called bleeding, and a second one for removing harvest from the bioreactor. The bleeding is performed to keep a steady concentration of cells inside the bioreactor, in order to maintain the biomass within the system's capacity and thereby maintain the cell viability. A cell retention device coupled to the second outflow channel clarifies the harvest stream, i.e. removes cells from the harvest stream, before sending the harvest stream to a separation device, such as a chromatography column (Bielser et al., Biotechnology Advances, 2018, 36: 1328-1340).

Although highly productive, the constant, slow, low-titer output from a perfusion bioreactor typically is no productivity challenge to a standard batch chromatography system dedicated to the bioreactor. However, to cope with the continuous product flow from the bioreactor, a surge tank will be required before the initial chromatography step in order to collect product during non-loading steps of the chromatography operation, adding to process complexity and also monitoring and validation requirements. Alternatively, downstream processing steps may be performed in continuous mode, with the aim to reduce chromatography system size and to avoid surge tank requirements. A multi-column system may provide the benefit of continuous loading, which has the potential to eliminate the need for a surge tank between the reactor and chromatography system, and may also allow a more compact chromatography system. However, a multi-column system also adds complexity to the process and use a larger number of columns, although smaller in size, than in a corresponding batch system.

Further, Mothes et al have described an alternative continuous purification strategy involving chromatographic steps that are performed continuously without intermediate holding times or process-fluid adjustments (Mothes et al., Bio-Process International, 2016, 14(5): 34-43, 58)

However, there is a continuous need in the art for improved methods for separation of biomolecules, comprising a simplified perfusion bioreactor process compared to prior art methods.

SUMMARY OF THE DISCLOSURE

An objective of the present disclosure is to provide an improved method for periodically removing harvest from a bioreactor and for separation, which solves or at least mitigates the problems described above. Said objective is achieved by the subject matter described herein, which relates to a method for separation of biomolecules by using optimized or regulated forwarding of product fluid from a perfusion bioreactor, in particular by pausing the product flow from the reactor during the time a first separation device is in non-loading mode, a mode that typically is relatively short compared to loading mode for the slow low-titer perfusion harvest. Thereby, a simplified yet productive and economic process design is achieved, using a traditional single chromatography column (or other separation device) in a batch capture step without the need for a surge tank after the bioreactor. Further, the relatively long capture cycle time resulting from the regulated output supports using a simple and robust traditional design of a following virus inactivation step as well as any further separation steps, alternatively called polishing steps. A control of the product fluid from the bioreactor will allow improvements in all aspects of the downstream process.

More particularly, a first aspect of the present disclosure is directed to a method 100 for separating a biomolecule from a fluid 2, wherein the biomolecule is produced by biological cells in a perfusion bioreactor 3, the method comprising:

forwarding (110) a product fluid comprising the biomolecule and biological cells from the perfusion bioreactor 3 during a bioreactor product output time period, $t_{BRp}$, which constitutes a first part of a bioreactor cycle time period, $t_{BR}$;

loading (210) a first separation device 4 with the product fluid obtained in step 110 during a first separation loading time period, $t_{S1l}$, which constitutes a first part of a first separation cycle time period $t_{S1}$;

pausing (130) the forwarding of the product fluid from the perfusion bioreactor during a bioreactor non-product output time period, $t_{BRn}$, which constitutes a second part of the bioreactor cycle time period; and pausing (220) the loading of the first separation device (4) during a second part of the first separation cycle time period, said second part comprising:

optionally a first separation wash time period, $t_{S1w}$, a first separation product elution time period, $t_{S1p}$, and a first separation regeneration time period, $t_{S1r}$;

wherein $$t_{BR} = t_{BRp} + t_{BRn},$$

$$t_{S1} >= t_{S1l} + t_{S1w} + t_{S1p} + t_{S1r},$$

and $$t_{BRn} >= t_{S1w} + t_{S1p} + t_{S1r};$$

repeating (150) steps 110, 210, 130, and 220 n times, wherein n is the number of times required to complete a production run.

According to a second aspect, the present disclosure provides a computer implemented method 600 performed by a controller configured to control a separation of a biomolecule from a fluid 2, wherein the biomolecule is produced by biological cells in a perfusion bioreactor 3, the method 600 comprising:

obtaining (610) measurement results by
    (i) performing (610a) a chemical, biochemical, and/or physical analysis of a fluid 2, and/or
    (ii) measuring (610b) a time period of performing at least a part of a method for separating the biomolecule, such as measuring the time period of at least a part of a bioreactor cycle or the time period of at least a part of a first separation cycle,
generating (620) control parameters based on the measurement results and a model, and
controlling (630) the separation of a biomolecule from a fluid 2 using the generated control parameters.

According to a third aspect, the present disclosure is directed to a controller 15, the controller 15 comprising:
    processing circuitry 16, and
    a memory 17, said memory 17 containing instructions executable by said processing circuitry 16, whereby said controller 15 is operative to perform any of the steps of the method according to the present disclosure.

According to a fourth aspect, the present disclosure is directed to computer program comprising computer-executable instructions for causing a controller 15, when the computer-executable instructions are executed on processing circuitry 16 comprised in the controller 15, to perform any of the steps of the method according to the present disclosure.

According to a fifth aspect, the present disclosure is directed to a computer program product comprising a computer-readable storage medium, the computer-readable storage medium having the computer program according to the present disclosure embodied therein.

Preferred aspects of the present disclosure are described below in the detailed description and in the dependent claims.

BRIEF DESCRIPTION OF THE DRAWINGS

FIG. 4 schematically shows a bioprocessing system including a controller for use in one or more embodiments of the presently disclosed method.

It should be appreciated that like reference numerals are used to identify like elements illustrated in one or more of the figures.

DETAILED DESCRIPTION OF THE DISCLOSURE

The working principle of the presently disclosed method allows removing harvest intermittently from the bioreactor. Possible strategies to achieve that could be e.g. maintaining the total number of cells constant in the bioreactor by means of bleeding out cells in a bleed stream, feeding at a constant cell specific feed rate and letting the volume increase when the harvest stream is paused and decrease in periods of harvest removal. However, other strategies can be applied for feed addition and harvest removal as well. One example could be alternating feed and harvest cycles, i.e. to pause the feed in the harvesting cycle and pause the harvest in the feed cycle.

Advantages of the presently disclosed method include that while the process is highly productive, the process has a simplistic, robust design and is easy to validate, and it requires a relatively small space for the bioreactor and separation devices, resulting in low capital expenses and operation expenses.

Figure 1:
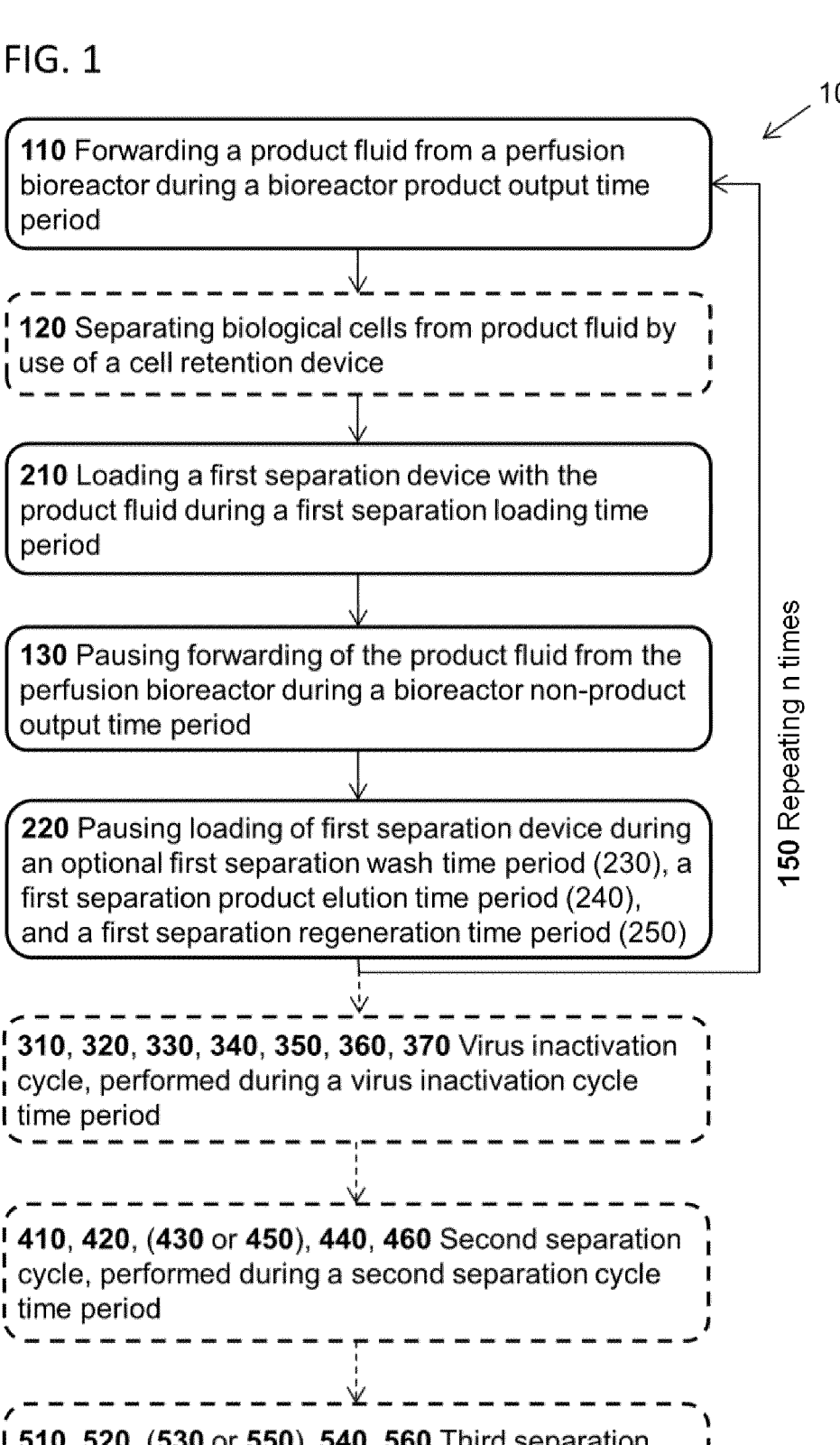
FIG. 1 is a flow chart of a method for separating a biomolecule according to the present disclosure.

The present disclosure according to a first aspect provides solves or at least mitigates the problems associated with existing methods for separating biomolecules by providing, as illustrated in the flow chart of FIG. 1, a method 100 for separating a biomolecule from a fluid 2, wherein the biomolecule is produced by biological cells in a perfusion bioreactor 3, the method comprising:

Step 110: forwarding a product fluid comprising the biomolecule and biological cells from the perfusion bioreactor 3 during a bioreactor product output time period, $t_{BRp}$, which constitutes a first part of a bioreactor cycle time period, $t_{BR}$;

Step 210: loading a first separation device 4 with the product fluid obtained in step 110 during a first separation loading time period, $t_{S1l}$, which constitutes a first part of a first separation cycle time period $t_{S1}$;

Step 130: pausing the forwarding of the product fluid from the perfusion bioreactor during a bioreactor non-product output time period, $t_{BRn}$, which constitutes a second part of the bioreactor cycle time period; and Step 220: pausing the loading of the first separation device 4 during a second part of the first separation cycle time period, said second part comprising: optionally a first separation wash time period, $t_{S1w}$, a first separation product elution time period, $t_{S1p}$, and a first separation regeneration time period, $t_{S1r}$; wherein $$t_{BR} = t_{BRp} + t_{BRn},$$

$$t_{S1} >= t_{S1f} + t_{S1w} + t_{S1p} + t_{S1r},$$

and $$t_{BRn} >= t_{S1w} + t_{S1p} + t_{S1r};$$

Step 150: repeating steps 110, 210, 130, and 220 n times, wherein n is the number of times required to complete a production run. In other words, n is the number of times required to complete the production of biomolecule by the biological cells. The production is complete when predetermined criteria set up for a complete production run have been fulfilled. The criteria may include the production time, the amount of biomolecule produced; the cell viability is below a critical value, etc.

Figure 2:
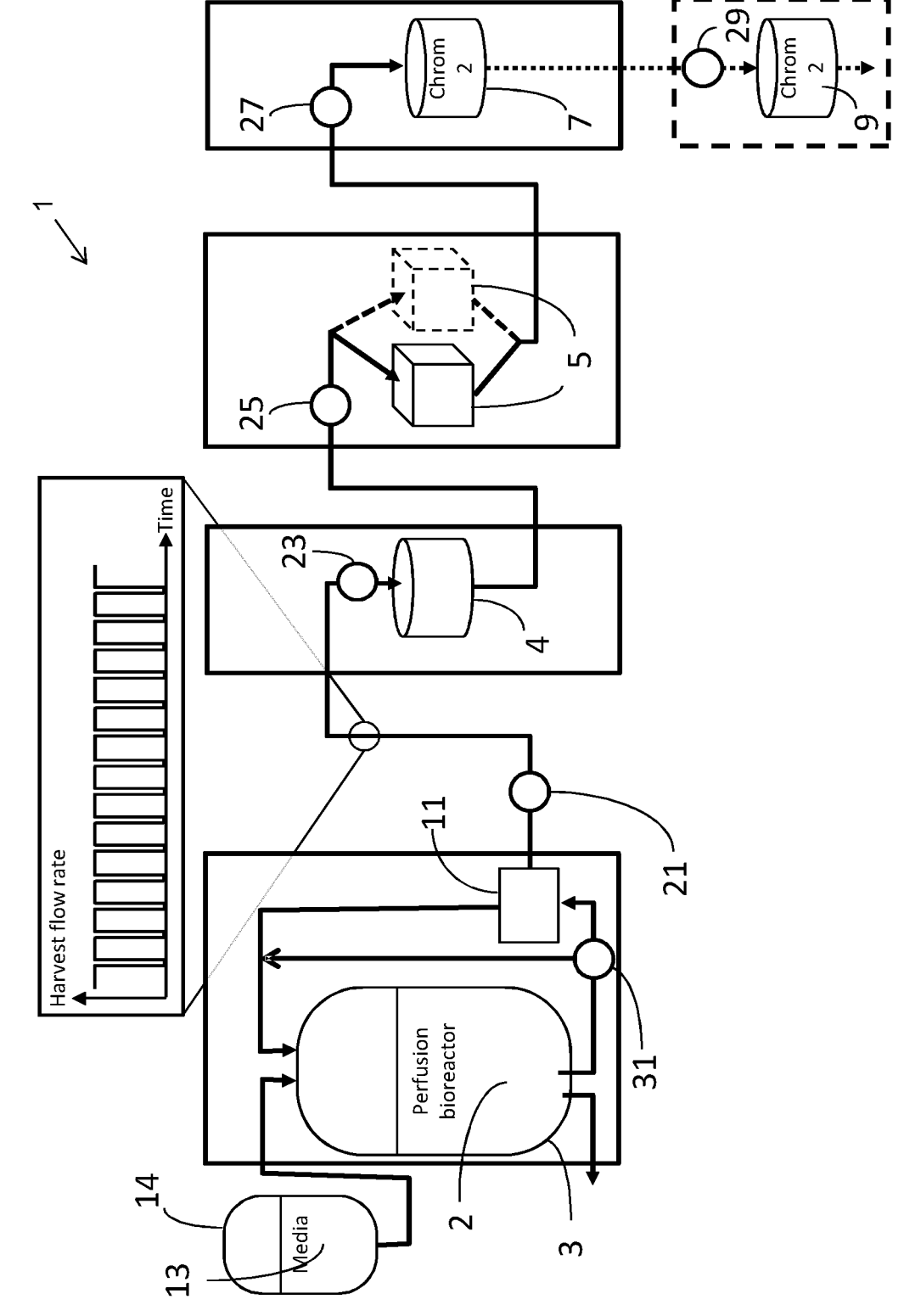
FIG. 2 schematically shows a bioprocessing system suitable for use in the presently disclosed method for separating a biomolecule.

The above-mentioned perfusion bioreactor 3 and the first separation device 4 are part of a bioprocessing system, further described in relation to FIG. 2.

The term "biomolecule" has its conventional meaning in the field of bioprocessing, in which biomolecules are produced (often recombinantly) by biological cells in a cell culture and purified from the cell culture by any means of separation and purification. Non-limiting examples of biomolecules are peptides and proteins, including but not limited to enzymes, antibodies and antibody fragments, as well as nucleic acid sequences, such as DNA and RNA. Herein, a biomolecule to be separated from a fluid by the presently disclosed method may alternatively be referred to as a "target biomolecule" or "target".

Herein, the term "biological cells" is intended to encompass any type of biological cells, such as bacterial cells, viral cells, fungal cells, insect cells, or mammalian cells. Biological cells are typically cultivated in a culture medium in a bioreactor. The mixture of culture medium, biological cells, products and by-products from the cell cultivation is herein often referred to as a "fluid", "product fluid", "product output fluid" or "product output". It is to be understood that these terms are used for fluid comprising the target biomolecule, which fluid is forwarded and/or otherwise processed at any phase or step of the presently disclosed method for separating biomolecules, in order to separate and purify the target biomolecule from the fluid.

The term "separation device" has its conventional meaning in the field of bioprocessing, and is to be understood as encompassing any type of separation device which is capable of and suitable for separating and purifying biomolecules from the fluid containing by-products from the production of the biomolecules. Non-limiting examples of a suitable first separation device for use in the presently disclosed method are a first chromatography column, a magnetic separator, a membrane adsorber, a monolith or a hydrogel. Non-limiting examples of chromatography columns suitable for use as a first separation device are columns packed with affinity chromatography resin, ion exchange chromatography resin, mixed mode chromatography resin or hydrophobic interaction chromatography resin.

In an embodiment, in which the first separation device is a first chromatography column, the first separation cycle time period is a first chromatography cycle time period, $t_{C1}$; the first separation loading time period is a first chromatography loading time period, $t_{C1l}$; the first separation wash time period is a first chromatography wash time period, $t_{C1w}$; the first separation product elution time period is a first chromatography product elution time period, $t_{C1p}$;

the first separation regeneration time period is a first chromatography regeneration time period, $t_{C1r}$;

$$t_{C1} >= t_{C1l} + t_{C1w} + t_{C1p} + t_{C1r};$$ and $$t_{BRn} >= t_{C1w} + t_{C1p} + t_{C1r}.$$

The above applies equally to embodiments in which the first separation device is a membrane adsorber, a monolith or a hydrogel instead of a chromatography column.

In step 110 of the presently disclosed method, the product fluid may optionally be forwarded to any type of device suitable for processing the product fluid before forwarding it further to the first separation device 4 to be loaded with the product fluid in step 210. For example, the product fluid may be forwarded to any type of cell retention device 11, for separating the biological cells from the product fluid (step 120). Cell retention devices are based on either cell size or density, and include filters (cross-flow, hollow fibers), centrifuges, gravity settlers, hydrocyclones or different geometry and acoustic wave separators (Bielser et al, 2018, as referred to above). In one presently preferred embodiment, the cell retention device used is a tangential filtration system, such as the alternating tangential flow (ATF) or the tangential flow filtration (TFF), both hollow fiber systems.

Further, the method may comprise recirculating (step 125) at least part of the biological cells to the perfusion bioreactor 3 after separating (step 120) the biological cells from the product fluid forwarded from the perfusion bioreactor 3.

Step 130 of the presently disclosed method may comprise:

Step 132a: pausing the flow of product fluid from the perfusion bioreactor 3, or Step 132b: pausing the flow of product fluid from the perfusion bioreactor 3 to the cell retention device 11, and optionally, wherein the cell retention device 11 is a filtering unit, back flushing (step 134) the filtering unit, or Step 132c: recirculating the product fluid to the perfusion bioreactor 3.

In step 132a and 132b respectively, the pausing of product fluid flow may be performed by a forwarding unit 21 configured to forward a product fluid from the perfusion bioreactor 3 and configured to pause the forwarding of a product fluid. The forwarding unit 21 may e.g. comprise one or more pumps, which may be switched on/off, and/or one or more valve units, which may be opened/closed, to control the flow of fluid from the perfusion bioreactor 3. Similarly, in step 132c, the recirculating of the product fluid to the perfusion bioreactor may be performed by the forwarding unit 31. Further, in step 132c the product fluid may pass through the cell retention device 11 before being recirculated or the product fluid may bypass the cell retention device 11 and be directly recirculated to the perfusion bioreactor 3, as illustrated in FIG. 2.

The presently disclosed method may comprise:

Step 160: removing a part of the biological cells from the perfusion bioreactor 3 without recirculating said part of the biological cells to the perfusion bioreactor 3, also known as bleeding. Such removing of said part of the biological cells may be performed during at least part of the time period $t_{BRn}$. The removing of cells may be done via an outlet from the perfusion bioreactor 3.

Alternatively or additionally, the removing of said part of the biological cells may be performed after separating the biological cells from the product fluid (i.e. step 120), meaning that cells may be removed via an outlet located after the cell retention device 11.

The presently disclosed method may comprise:

Step 170: feeding culture medium 13 to the perfusion bioreactor 3 during the entire bioreactor cycle time period, $t_{BR}$, optionally wherein the flow rate of culture medium to the perfusion bioreactor, $F_{in}$, is constant throughout the steps 110 and 130. The forwarding of product fluid in step 110 is performed at a flow rate out of the perfusion bioreactor, $F_{out}$, wherein $F_{out}$ is substantially equal to $(F_{in}*(t_{S1}/t_{S1l}))$.

The term "bioreactor product output time period" is to be understood as the time period during which product fluid is allowed to exit the bioreactor. Hence, during this time period the product fluid may be forwarded to a subsequent device in a bioprocessing system, further described in relation to FIG. 2. In contrast, the term "bioreactor non-product output time period" is intended to mean the time period during which product fluid is not allowed to exit the bioreactor, and hence cannot be forwarded from the bioreactor to a subsequent device in the bioprocessing system. However, when the system changes from product output mode to non-product output mode the last part of the product fluid exiting the bioreactor may still be remaining in a flow channel between the bioreactor and a subsequent device. It is to be understood that such product fluid which has already exited the bioreactor but is still remaining in a flow channel may be forwarded to the subsequent device during a bioreactor non-product output time period in order to completely empty the flow channel from product fluid.

Further, it is to be understood that the bioreactor product output time period, as well as any other herein mentioned time period comprising forwarding of product fluid from one device to a subsequent device in the bioprocessing system, may comprise brief pauses or breaks in product output due to brief pausing or stopping of the exiting of product fluid from the bioreactor or any other device. Such brief pauses may be included during a product output time period if there is an immediate need for pausing, such as in case any adjustments of the bioprocessing system are called for, for example if any type of system maintenance is required, e.g. switching to a new cell retention device (e.g. hollow fiber filter switch after fouling), or replacing an empty buffer container with a new buffer container. After such a short break, the exiting of product fluid from the device is resumed. The product output time period continues during the short break as well as during the resumed exiting of product fluid. It is to be understood that the inclusion of any such called-for brief pauses during a product output time period may be done without departing from the overall concept of the presently disclosed method.

Further, the first separation cycle may comprise brief pauses or breaks between one or several of the steps of the cycle. Hence, the first separation cycle time period is larger than or equal to the sum of the first separation loading time period, the first separation wash time period, the first separation product elution time period and the first separation regeneration time period, i.e. $t_{S1} \geq t_{S1l}+t_{S1w}+t_{S1p}+t_{S1r}$. This may alternatively be described as $t_{S1}=t_{S1l}+t_{S1w}+t_{S1p}+t_{S1r}+t_{S1b}$, wherein $t_{S1b}$, is a first separation break time period. Consequently, $T_{BRn} \geq t_{S1w}+t_{S1p}+t_{S1r}$ may alternatively be described as $t_{BRn}=t_{S1w}+t_{S1p}+t_{S1r}+t_{S1b}$, wherein $t_{S1b}$ is the first separation break time period. In non-limiting examples of the method, the first separation break time period may constitute from 0% to about 30% of the entire first separation cycle time period.

Also, it is to be understood that the first separation loading time period, as well as any other herein mentioned time period comprising loading or filling a device with product fluid, may comprise brief pauses or breaks in loading or filling of product fluid. Such brief pauses may be included during a loading/filling time period if there is an immediate need for pausing, such as in case any adjustments of the bioprocessing system are required, as exemplified above. After such a short break, the loading or filling of the device with product fluid is resumed. The loading/filling time period continues during the short break as well as during the resumed loading/filling of product fluid. It is to be understood that the inclusion of any such called-for brief pauses during a loading/filling time period may be done without departing from the overall concept of the presently disclosed method.

According to the presently disclosed method, the forwarding of the product fluid from the perfusion bioreactor (step 110) and the loading of the first separation device 4 with the product fluid (step 210) may preferably be performed substantially simultaneously. This means that the first separation loading time period may preferably occur substantially simultaneously as the bioreactor product output time period. Thus, steps 110 and 210 may preferably be performed essentially at the same time, or more preferably simultaneously or exactly at the same time, i.e. $t_{S1l}=t_{BRp}$. However, although the aim may be to perform steps 110 and 210 simultaneously it is to be understood that the length of said two time periods may differ, for example due to the time it takes to transport the fluid in the flow channels from the bioreactor 3 to the first separation device 4, including possible intermediate devices, or due to short breaks for adjustments in the system.

Further, the second part of the first separation cycle time period mentioned above in relation to step 220 may comprise:

Step 230: optionally causing a washing liquid to pass through the first separation device 4 during the optional first separation wash time period, Step 240: forwarding a product fluid from the first separation device 4 during the first separation product elution time period, and Step 250: regenerating the first separation device 4 during the first separation regeneration time period.

As shown in the flow chart of FIG. 1, the presently disclosed method may further comprise a virus inactivation cycle, performed during a virus inactivation cycle time period, $t_{VI}$, following the first separation cycle.

In particular, a virus inactivation cycle may comprise:

Step 310: filling a virus inactivation vessel 5 during a virus inactivation fill time period, $t_{VIf}$, with the product fluid obtained from the first separation cycle.

The virus inactivation cycle may further comprise:

Step 320: decreasing the pH during a virus inactivation pH decrease time period, $t_{VId}$, Step 330: holding the decreased pH during a virus inactivation decreased pH hold time period, $t_{VIh}$, Step 340: increasing the pH and adjusting the buffer during a virus inactivation pH increase and buffer adjustment time period, $t_{VIi}$, Step 350: forwarding a product fluid from the virus inactivation vessel 5 during a virus inactivation product output time period $t_{VIp}$, and Step 360: optionally regenerating the virus inactivation vessel 5 during a virus inactivation regeneration time period $t_{VIr}$. Regeneration of the virus inactivation vessel 5 may comprise washing or rinsing the vessel 5.

Herein, a "vessel" may for example be a tank, a bag or other hollow container suitable to hold a liquid.

It is to be understood that virus inactivation may be achieved by other techniques known in the art of virus inactivation. Instead of decreasing, holding and increasing the pH in steps as described above, virus inactivation may for example be achieved by use of a so-called solvent/detergent method or any other suitable method (see WHO Technical Report, Series No. 924, 2004; https://www.who.int/bloodproducts/publications/WHO_TRS_924_A4.pdf)

According to the presently disclosed method, the forwarding of the product fluid from the first separation device 4 (step 240) and the filling of the virus inactivation vessel 5 (step 310) with said product fluid are preferably performed substantially simultaneously. This means that the first separation elution time period may preferably occur substantially simultaneously as the virus inactivation fill time period. Thus, steps 240 and 310 may preferably be performed essentially at the same time, or more preferably simultaneously or exactly at the same time, i.e. $t_{S1p}=t_{VIf}$. However, although the aim may be to perform steps 240 and 310 simultaneously it is to be understood that the length of said two time periods may differ, for example due to the time it takes to transport the fluid in the flow channels from the first separation device 4 to the virus inactivation vessel 5, or due to short breaks for adjustments in the system.

Further, $t_{VI}=t_{VIf}+t_{VId}+t_{VIh}+t_{VIi}+t_{VIp}$+optionally $t_{VIr}$; meaning that if step 360 is performed, the virus inactivation regeneration time period $t_{VIr}$ is included in the virus inactivation cycle time period, such that $t_{VI}=t_{VIf}t_{VId} t_{VIh}+t_{VIi}+t_{VIp}+t_{VIr}$.

In contrast, if step 360 is not performed, $t_{VI}=t_{VIf}+t_{VId}+t_{VIh}+t_{VIi} t_{VIp}$.

Further, $t_{BR}-t_{S1p}>=t_{VId}+t_{VIh}+t_{VIi}+t_{VIp}$+optionally $t_{VIr}$; meaning that if step 360 is performed, $$t_{BR}-t_{S1p}>=t_{VId}+t_{VIh}+t_{VIi}+t_{VIp}+t_{VIr}.$$

In contrast, if step 360 is not performed, $t_{BR}-t_{S1p}>=t_{VId}+t_{VIh}+t_{VIi}+t_{VIp}$.

In an embodiment, step 310 may comprise:

Step 310a: alternatingly filling two virus inactivation vessels 5 during the virus inactivation fill time period, $t_{VIf}$, with the product fluid obtained from the first separation cycle;

wherein the forwarding of the product fluid from the first separation device 4 (step 240) and the alternating filling of the two virus inactivation vessels 5 (step 310a) with said product fluid are performed substantially simultaneously. Further, $t_{VI}=t_{VIf}+t_{VId}+t_{VIh}+t_{VIi}+t_{VIp}$+optionally $t_{VIr}$; and $$2t_{BR}-t_{S1p}>=t_{VId}+t_{VIh}+t_{VIi}+t_{VIp}+\text{optionally } t_{VIr}>=t_{BR}-t_{S1p}$$

If step 360 is performed in this embodiment, $t_{VI}=t_{VIf}+t_{VId}+t_{VIh}+t_{VIi}+t_{VIp}+t_{VIr}$; and $2t_{BR}-t_{S1p}>=t_{VId}+t_{VIh}+t_{VIi}+t_{VIp}+t_{VIr}>=t_{BR}-t_{S1p}$.

In contrast, if step 360 is not performed, $t_{VI}=t_{VIf}+t_{VId}+t_{VIh}+t_{VIi}+t_{VIp}$; and $2t_{BR}-t_{S1p}>=t_{VId}+t_{VIh}+t_{VIi}+t_{VIp}>=t_{BR}-t_{S1p}$.

Alternatively or additionally, step 310 may comprise:

Step 310b: filling the virus inactivation vessel(s) 5 during the virus inactivation fill time period with product fluid obtained from two or more of the first separation cycle.

The presently disclosed method may further comprise:

Step 370: repeating the virus inactivation cycle n times or less. It is to be understood that normally, the virus inactivation cycle is performed as many times as the bioreactor cycle and the first separation cycle are performed. However, if the virus inactivation vessel(s) 5 is/are filled with product fluid obtained from two or more of the first separation cycle, the number of times the virus inactivation cycle has to be repeated decreases correspondingly. Alternatively, instead of performing virus inactivation in the above-described batch mode, the virus inactivation of the product fluid may be performed in continuous mode. In the latter case, the virus inactivation cycle time period would extend over many or all of the bioreactor cycle time periods and over many or all of the first separation cycle time periods, and thus it would not be relevant to repeat the virus inactivation cycle n times or even any time.

As shown in the flow chart of FIG. 1, the presently disclosed method may further comprise a second separation cycle, performed during a second separation cycle time period, $t_{S2}$, following the virus inactivation cycle, wherein $t_{BR}>=t_{S2}$.

In the presently disclosed method, it is preferable that a virus inactivation cycle is performed after the first separation cycle and before a second separation cycle. One reason is that the pH of the product fluid would normally have a low pH when exiting the first separation device, which matches step 320 at the beginning of the virus inactivation cycle, since step 320 comprises decreasing the pH of the product fluid. Also, the virus inactivation vessel may function as a hold tank between the first separation cycle and the second separation cycle, in case this would be required, for example for making adjustments in the system.

In particular, a second separation cycle may comprise a bind-elute type of separation:

Step 410: loading a second separation device 7 with the product fluid obtained from the virus inactivation cycle, during a second separation loading time period, $t_{S2l}$, which constitutes a first part of the second separation cycle time period, wherein the forwarding of the product fluid from the virus inactivation vessel 5 (step 350) and the loading of the second separation device 7 with said product fluid (step 410) are performed substantially simultaneously. This means that the virus inactivation product output time period may preferably occur substantially simultaneously as the second separation loading time period. Thus, steps 350 and 410 may preferably be performed essentially at the same time, or more preferably simultaneously or exactly at the same time, i.e. $t_{VIp}=t_{S2l}$. However, although the aim may be to perform steps 350 and 410 simultaneously, it is to be understood that the length of said two time periods may differ, for example due to the time it takes to transport the fluid in the flow channels from the virus inactivation vessel 5 to the second separation device 7, or due to short breaks for adjustments in the system.

The second separation cycle may further comprise, during a second part of the second separation cycle time period:

Step 420: optionally causing a washing liquid to pass through the second separation device 7 during a second separation wash time period, $t_{S2w}$, Step 430: forwarding a product fluid from the second separation device 7 during a second separation product elution time period, $t_{S2p}$, and Step 440: regenerating the second separation device 7 during a second separation regeneration time period, $t_{S2r}$;

wherein $t_{S2} >= t_{S2l} + t_{S2w} + t_{S2p} + t_{S2r}$.

It is to be understood that the second separation cycle may comprise pauses or breaks between one or several of the steps of the cycle, e.g. for system maintenance. Hence, the second separation cycle time period is larger than or equal to the sum of the second separation loading time period, the second separation wash time period, the second separation product elution time period and the second separation regeneration time period, i.e. $t_{S2} >= t_{S2l} + t_{S2w} + t_{S2p} + t_{S2r}$. This may alternatively be described as $t_{S2} = t_{S2l} + t_{S2w} + t_{S2p} + t_{S2r} + t_{S2b}$, wherein $t_{S2b}$, is a second separation break time period.

According to an alternative embodiment, the second separation cycle may comprise a flow-through type of separation:

Step 450: causing the product fluid obtained from the virus inactivation cycle to flow through the second separation device 7 during a second separation flow through time period, $t_{S2l}$, and Step 440: regenerating the second separation device 7 during a second separation regeneration time period, $t_{S2r}$;

wherein $t_{S2} >= t_{S2l} + t_{S2r}$, which may alternatively be described as $t_{S2} = t_{S2l} + t_{S2r} + t_{S2b}$, wherein $t_{S2b}$, is a second separation break time period, and wherein the forwarding of the product fluid from the virus inactivation vessel 5 (step 350) and the causing of said product fluid to flow through the second separation device 7 (step 450) are performed substantially simultaneously. This means that the virus inactivation product output time period may preferably occur substantially simultaneously as the second separation flow through time period. Thus, steps 350 and 450 may preferably be performed essentially at the same time, or more preferably simultaneously or exactly at the same time, i.e. $t_{VIp} = t_{S2l}$. However, although the aim may be to perform steps 350 and 410 simultaneously, it is to be understood that the length of said two time periods may differ, for example due to the time it takes to transport the fluid in the flow channels from the virus inactivation vessel 5 to the second separation device 7, or due to short breaks for adjustments in the system.

Non-limiting examples of a suitable second separation device 7 for use in the presently disclosed method are a chromatography column, a membrane adsorber, a monolith, or a hydrogel. Non-limiting examples of chromatography columns suitable for use as a second separation device are columns packed with ion exchange chromatography resin, mixed mode chromatography resin or hydrophobic interaction chromatography resin.

In an embodiment, in which the second separation device is a second chromatography column, the second separation loading time period is a second chromatography loading time period, $t_{C2l}$;

the second separation cycle time period is a second chromatography cycle time period, $t_{C2}$;

the second separation wash time period is a second chromatography wash time period, $t_{C2w}$;

the second separation product elution time period is a second chromatography product elution time period, $t_{C2p}$;

the second separation regeneration time period is a second chromatography regeneration time period, $t_{C2r}$;

$t_{BR} >= t_{C2}$;

$t_{C2l} = t_{VIp}$; and $t_{C2} >= t_{C2l} + t_{C2w} + t_{C2p} + t_{C2r}$.

The above applies equally to embodiments in which the second separation device is a membrane adsorber, a monolith or a hydrogel instead of a chromatography column.

The presently disclosed method may further comprise:

Step 460: repeating the second separation cycle n times. Alternatively, the second separation cycle may be performed less than n times, for example if output from several first separation cycles and/or output from several virus inactivation cycles are pooled before the second separation device is loaded with said pooled outputs.

As shown in the flow chart of FIG. 1, the presently disclosed method may further comprise a third separation cycle, performed during a third separation cycle time period, $t_{S3}$, following the second separation cycle, wherein $t_{BR} >= t_{S3}$.

In particular, a third separation cycle may comprise a bind-elute type of separation:

Step 510: loading a third separation device 9 with a product fluid obtained from the second separation cycle, during a third separation loading time period, $t_{S3l}$, which constitutes a first part of the third separation cycle time period $t_{S3}$, wherein the forwarding of said product fluid from the second separation device 7 (step 430), or the causing of said product fluid to flow through the second separation device 7 (step 450), and the loading of the third separation device 9 with said product fluid (step 510) are performed substantially simultaneously. This means that the second separation product elution time period, or alternatively the second separation flow through time period, may preferably occur substantially simultaneously as the third separation loading time period. Thus, step 430 or 450 may preferably be performed essentially at the same time as step 510, or more preferably simultaneously or exactly at the same time, i.e. $t_{S2p} = t_{S3l}$ or $t_{S2l} = t_{S3l}$. However, although the aim may be to perform step 430/450 and step 510 simultaneously, it is to be understood that the length of said two time periods may differ, for example due to the time it takes to transport the fluid in the flow channels from the second separation device 7 to the third separation device 9, or due to short breaks for adjustments in the system.

The third separation cycle may further comprise, during a second part of the third separation cycle time period:

Step 520: optionally causing a washing liquid to pass through the third separation device 9 during a third separation wash time period, $t_{S3w}$, Step 530: forwarding a product fluid from the third separation device 9 during a third separation product elution time period, $t_{S3p}$, and Step 540: regenerating the third separation device 9 during a third separation regeneration time period, $t_{S3r}$;

wherein $t_{S3} >= t_{S3l} + t_{S3w} + t_{S3p} + t_{S3r}$.

It is to be understood that the third separation cycle may comprise pauses or breaks between one or several of the steps of the cycle, e.g. for system maintenance. Hence, the third separation cycle time period is larger than or equal to the sum of the third separation loading time period, the third separation wash time period, the third separation product elution time period and the third separation regeneration time period (i.e. $t_{S3} \geq t_{S3l} + t_{S3w} + t_{S3p} + t_{S3r}$). This may alternatively be described as $t_{S3} = t_{S3l} + t_{S3w} + t_{S3p} + t_{S3r} + t_{S3b}$, wherein $t_{S3b}$, is a third separation break time period.

According to an alternative embodiment, the third separation cycle may comprise a flow-through type of separation:

Step 550: causing a product fluid obtained from the second separation cycle to flow through the third separation device 9 during a third separation flow through time period, $t_{S3l}$, and Step 540: regenerating the third separation device 9 during a third separation regeneration time period, $t_{S3r}$;

wherein $t_{S3} \geq t_{S3l} + t_{S3r}$, which may alternatively be described as $t_{S3} = t_{S3l} + t_{S3r} + t_{S3b}$, wherein $t_{S3b}$, is a third separation break time period, and wherein the forwarding of said product fluid from the second separation device 7 (step 430), or the causing of said product fluid to flow through the second separation device 7 (step 450) and the causing of said product fluid to flow through the third separation device 9 (step 550) are performed substantially simultaneously. This means that the second separation product elution time period, or alternatively the second separation flow through time period, may preferably occur substantially simultaneously as the third separation flow through time period. Thus, step 430 or 450 may preferably be performed essentially at the same time as step 550, or more preferably simultaneously or exactly at the same time, i.e. $t_{S2p} = t_{S3l}$ or $t_{S2l} = t_{S3l}$. However, although the aim may be to perform step 430/450 and step 550 simultaneously or substantially simultaneously, it is to be understood that the length of said two time periods may differ, for example due to the time it takes to transport the fluid in the flow channels from the second separation device 7 to the third separation device 9, and/or due to short breaks for adjustments in the system, such as adjustment of buffer(s) between the second and third separation devices.

Non-limiting examples of a suitable third separation device 9 for use in the presently disclosed method are a chromatography column, a membrane adsorber, a monolith, or a hydrogel. Non-limiting examples of chromatography columns suitable for use as a second separation device are columns packed with ion exchange chromatography resin, mixed mode chromatography resin or hydrophobic interaction chromatography resin.

In an embodiment, in which the third separation device is a third chromatography column, the third separation loading time period is a third chromatography loading time period, $t_{C3l}$;

the third separation cycle time period is a third chromatography cycle time period, $t_{C3}$;

the third separation wash time period is a third chromatography wash time period, $t_{C3w}$;

the third separation product elution time period is a third chromatography product elution time period, $t_{C3p}$;

the third separation regeneration time period is a third chromatography regeneration time period, $t_{C3r}$;

$$t_{BR} \geq t_{C3};$$

$$t_{C3l} = t_{C2p}; \text{ and}$$

$$t_{C3} \geq t_{C3l} + t_{C3w} + t_{C3p} + t_{C3r}.$$

The above applies equally to embodiments in which the third separation device is a membrane adsorber, a monolith or a hydrogel instead of a chromatography column.

The presently disclosed method may further comprise:

Step 560: repeating the third separation cycle n times. Alternatively, the third separation cycle may be performed less than n times, for example if output from several first separation cycles and/or output from several virus inactivation cycles and/or output from several second separation cycles are pooled before the third separation device is loaded with said pooled outputs.

In the presently disclosed method, the first separation wash time period, if any, may comprise causing a washing liquid to pass through the first separation device 4 and repeating said step at least once. Alternatively or additionally, a second separation wash time period, if any, may comprise causing a washing liquid to pass through the second separation device 7 and repeating said step at least once. Alternatively or additionally, a third separation wash time period, if any, may comprise causing a washing liquid to pass through the third separation device 9 and repeating said step at least once.

Further, according to the presently disclosed method:

the complete production run may be performed during a time period, $t_{PR}$, which is in a range of from about 10 days to about 60 days, such as from about 20 days to about 50 days, such as from about 30 days to about 40 days, or about 10, 15, 20, 25, 30, 35, 40, 45, 50, 55, or 60 days;

n is an integer which may be in a range of from about 20 to about 300, such as about 20, 30, 40, 50, 60, 70, 80, 90, 100, 150, 200, 250, or 300;

$t_{S1}$ may be in a range of from about 2.5 to about 24 hours, such as about 2.5, 3, 4, 5, 6, 7, 8, 9, 10, 11, 12, 13, 14, 15, 16, 17, 18, 19, 20, 21, 22, 23, or 24 hours;

provided that $t_{PR} = n * t_{S1}$.

FIG. 2 schematically shows a non-limiting example of a bioprocessing system 1, which may be used to perform the method 100 according to the present disclosure. The bioprocessing system 1 comprises a perfusion bioreactor 3, which may contain a fluid 2 comprising biological cells cultured to produce any type of target biomolecule. The perfusion bioreactor 3 has two or more inlets and two or more outlets. Culture medium 13 from a culture medium container 14 may be provided to the perfusion bioreactor 3 via a first inlet. Biological cells may be removed from the bioreactor 3 via a first outlet. Product fluid may exit the bioreactor 3 via a second outlet, and may be forwarded via a forwarding unit 31 to a cell retention device 11 as shown in FIG. 2. Examples of different types of cell retention devices which may be used in the bioprocessing system 1 have been given above in connection with FIG. 1. However, it is to be understood that the cell retention device 11 is an optional component of the system 1. Biological cells which are to be recirculated to the perfusion bioreactor 3 after separation from the product fluid may be recirculated via the cell retention device 11 and added to the bioreactor 3 via a second inlet. Product fluid which is to be recirculated to the perfusion bioreactor 3 may be recirculated via the cell retention device 11 or directly via the forwarding unit 31 (i.e. by-passing the cell retention device 11), and added to the bioreactor 3 via the second inlet (as shown in FIG. 2) or via a third outlet (not shown). In an embodiment in which the cell retention device 11 is a TFF/hollow fiber filter, there is no need for the bypass channel from forwarding unit 31 to the bioreactor 3 as shown in FIG. 2. The forwarding unit 31 is typically a pump.

The bioreactor 3 is connected to a first separation device 4, either directly or via a cell retention device 11 or any other type of intermediate device suitable for processing of the product fluid before loading the first separation device 4 with the product fluid. The first separation device 4 is further connected to at least one virus inactivation vessel 5. FIG. 2 shows two virus inactivation vessels 5, wherein one is optional as illustrated by the dotted lines. The at least one virus inactivation vessel 5 is connected to a second separation device 7, which in turn may be connected to a third separation device 9.

The bioprocessing system 1 further comprises a first controllable forwarding unit 21 configured to forward a product fluid from the perfusion bioreactor 3 and configured to pause the forwarding of a product fluid in response to received control signals. The first controllable forwarding unit 21 may e.g. comprise one or more pumps and/or one or more valve units, such as electrically controlled pumps or valve units configured to control the flow of fluid from the perfusion bioreactor by, at least partially, switching on/off one or more pumps and/or opening/closing one or more valves in response to the control signals. The bioprocessing system 1 further comprises a first controllable loading unit 23 configured to load a first separation device 4 with a product fluid and configured to pause the loading of the first separation device 4. The first controllable loading unit 23 may e.g. comprise one or more pumps and/or one or more valve units configured to control the flow of fluid to the first separation device by, at least partially, switching on/off one or more pumps and/or opening/closing one or more valves in response to the control signals.

The bioprocessing system 1 may further comprise a second controllable loading/filling unit 25 configured to fill a virus inactivation vessel 5 with a product fluid and configured to pause the filling of the virus inactivation vessel 5 in response to received control signals. Alternatively, the second controllable loading/filling unit 25 may be configured to alternatingly fill two virus inactivation vessels 5 with a product fluid and configured to pause the alternating filling of the virus inactivation vessels 5 in response to received control signals. The second controllable loading/filling unit 25 may e.g. comprise one or more pumps and/or one or more valve units configured to control the flow of fluid to the virus inactivation vessel(s) 5 by, at least partially, switching on/off one or more pumps and/or opening/closing one or more valves in response to the control signals.

The bioprocessing system 1 may further comprise a third controllable loading unit 27 configured to load a second separation device 7 with a product fluid and configured to pause the loading of the second separation device 7. The third controllable loading unit 27 may e.g. comprise one or more pumps and/or one or more valve units configured to control the flow of fluid to the second separation device 7 by, at least partially, switching on/off one or more pumps and/or opening/closing one or more valves in response to the control signals.

The bioprocessing system 1 may further comprise a fourth controllable loading unit 29 configured to load a third separation device 9 with a product fluid and configured to pause the loading of the third separation device 9. The fourth controllable loading unit 29 may e.g. comprise one or more pumps and/or one or more valve units configured to control the flow of fluid to the third separation device 9 by, at least partially, switching on/off one or more pumps and/or opening/closing one or more valves in response to the control signals.

The bioprocessing system 1 may further comprise a second controllable forwarding unit (not shown in FIG. 2) configured to forward a product fluid from the first separation device 4 and configured to pause the forwarding of the product fluid from the first separation device 4 in response to received control signals. The bioprocessing system 1 may further comprise a third controllable forwarding unit (not shown in FIG. 2) configured to forward a product fluid from the virus inactivation vessel(s) 5 and configured to pause the forwarding of the product fluid from the virus inactivation vessel(s) 5 in response to received control signals. The bioprocessing system 1 may further comprise a fourth controllable forwarding unit (not shown in FIG. 2) configured to forward a product fluid from the second separation device 7 and configured to pause the forwarding of the product fluid from the second separation device 7 in response to received control signals. The bioprocessing system 1 may further comprise a fifth controllable forwarding unit (not shown in FIG. 2) configured to forward a product fluid from the third separation device 9 and configured to pause the forwarding of the product fluid from the third separation device 9 in response to received control signals. Such second, third, fourth, and/or fifth controllable forwarding units may e.g. comprise one or more pumps and/or one or more valve units configured to control the forwarding of fluid from each device, respectively, by, at least partially, switching on/off one or more pumps and/or opening/closing one or more valves in response to the control signals.

It is to be understood that the bioprocessing system 1 may further comprise other controllable units, such as controllable flow units configured to control the flow of washing liquid(s) and/or buffering liquid(s) and/or regenerating liquid(s) in any part(s) of the bioprocessing system 1 in response to received control signals. Such controllable flow units may e.g. comprise one or more pumps and/or one or more valve units configured to control the flow of liquid by, at least partially, switching on/off one or more pumps and/or opening/closing one or more valves in response to the control signals.

The presently disclosed method may be performed in a system, which comprises one or more single-use (presterilized and disposable) components, such as a single-use perfusion bioreactor, a single-use cell retention device, a single-use first separation device, single-use flow channels, or combinations thereof.

The above-described method may be at least in part a computer-implemented method 600 performed by a controller 15 configured to:

Step 630: control a separation of a biomolecule from a fluid 2.

The controlling (step 630) may comprise:

Step 640: controlling a first forwarding unit 21 to forward the product fluid from the perfusion bioreactor 3 (i.e. step 110 mentioned above), Step 650: controlling a first loading unit 23 to load the first separation device 4 with the product fluid (i.e. step 210 described above), Step 660: controlling the first forwarding unit 21 to pause the forwarding of product fluid from the perfusion bioreactor 3 (i.e. step 130 mentioned above), and/or Step 670: controlling the first loading unit 23 to pause the loading of the first separation device 4 (i.e. step 220 described above).

In order to run a perfusion system with a single first separation device system and eliminate the need for a surge tank after the reactor, one could match the elution and regeneration phases in the first separation device with pauses in output from the bioreactor, preferably using a control system connecting the bioreactor, harvest module and separation device.

Figure 3:
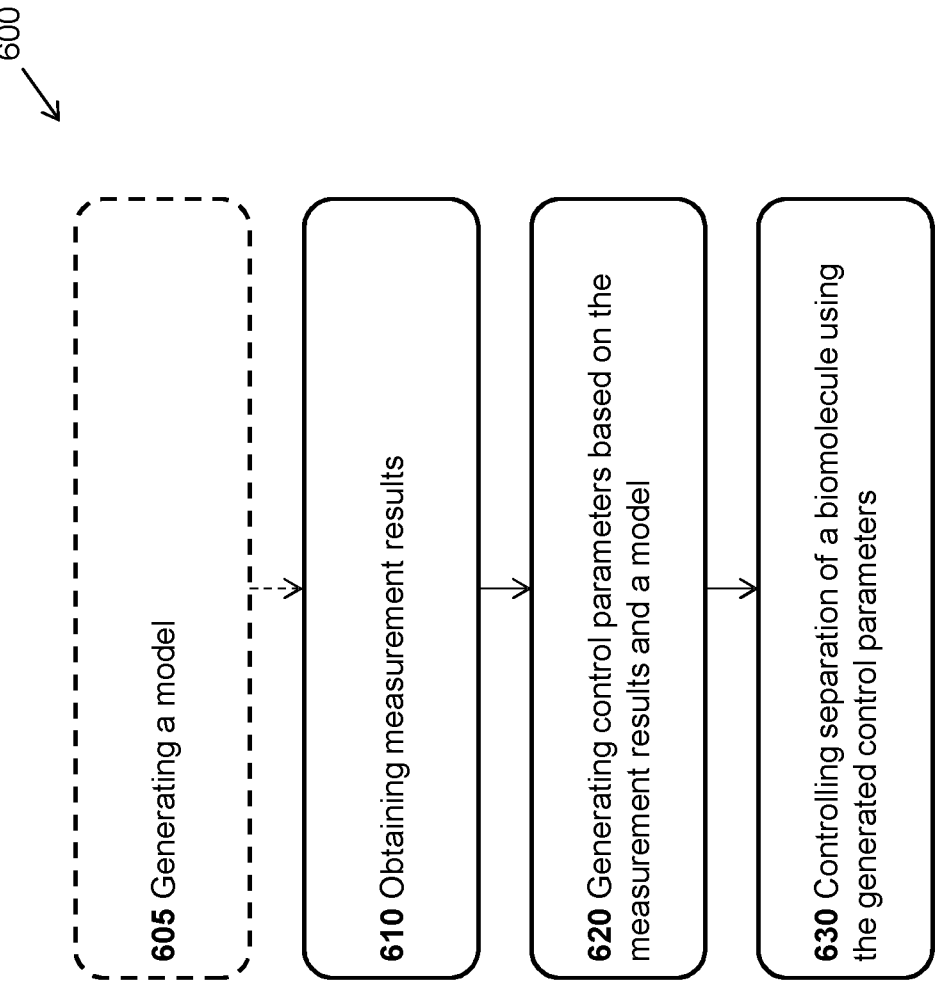
FIG. 3 is a flow chart of a computer-implemented method performed by a controller configured to control a method for separating a biomolecule according to the present disclosure.

Accordingly, as illustrated by the flow chart in FIG. 3, in a second aspect the present disclosure provides a computer-implemented method 600 performed by a controller 15 configured to control a separation of a biomolecule from a fluid 2, wherein the biomolecule is produced by biological cells in a perfusion bioreactor 3, the method 600 comprising:

Step 610: obtaining measurement results by (i) Step 610*a*: performing a chemical, biochemical, and/or physical analysis of a fluid 2, and/or (ii) Step 610*b*: measuring a time period of performing at least a part of a method for separating the biomolecule, such as measuring the time period of at least a part of a bioreactor cycle or the time period of at least a part of a first separation cycle, Step 620: generating control parameters based on the measurement results and a model, and Step 630: controlling the separation of a biomolecule from a fluid 2 using the generated control parameters.

In relation to the computer-implemented method 600, the controller 15 may be configured to control any one or more steps of the above-described method 100 for separating a biomolecule from a fluid 2.

According to the second aspect of the present disclosure, step 630 of the computer-implemented method 600 may comprise:

Step 640: controlling a first forwarding unit 21 to forward the product fluid from the perfusion bioreactor 3 (i.e. step 110 mentioned above), Step 650: controlling a first loading unit 23 to load the first separation device 4 with the product fluid (i.e. step 210 described above), Step 660: controlling the first forwarding unit 21 to pause the forwarding of product fluid from the perfusion bioreactor 3 (i.e. step 130 mentioned above), and/or Step 670: controlling the first loading unit 23 to pause the loading of the first separation device 4 (i.e. step 220 described above).

Figure 4:
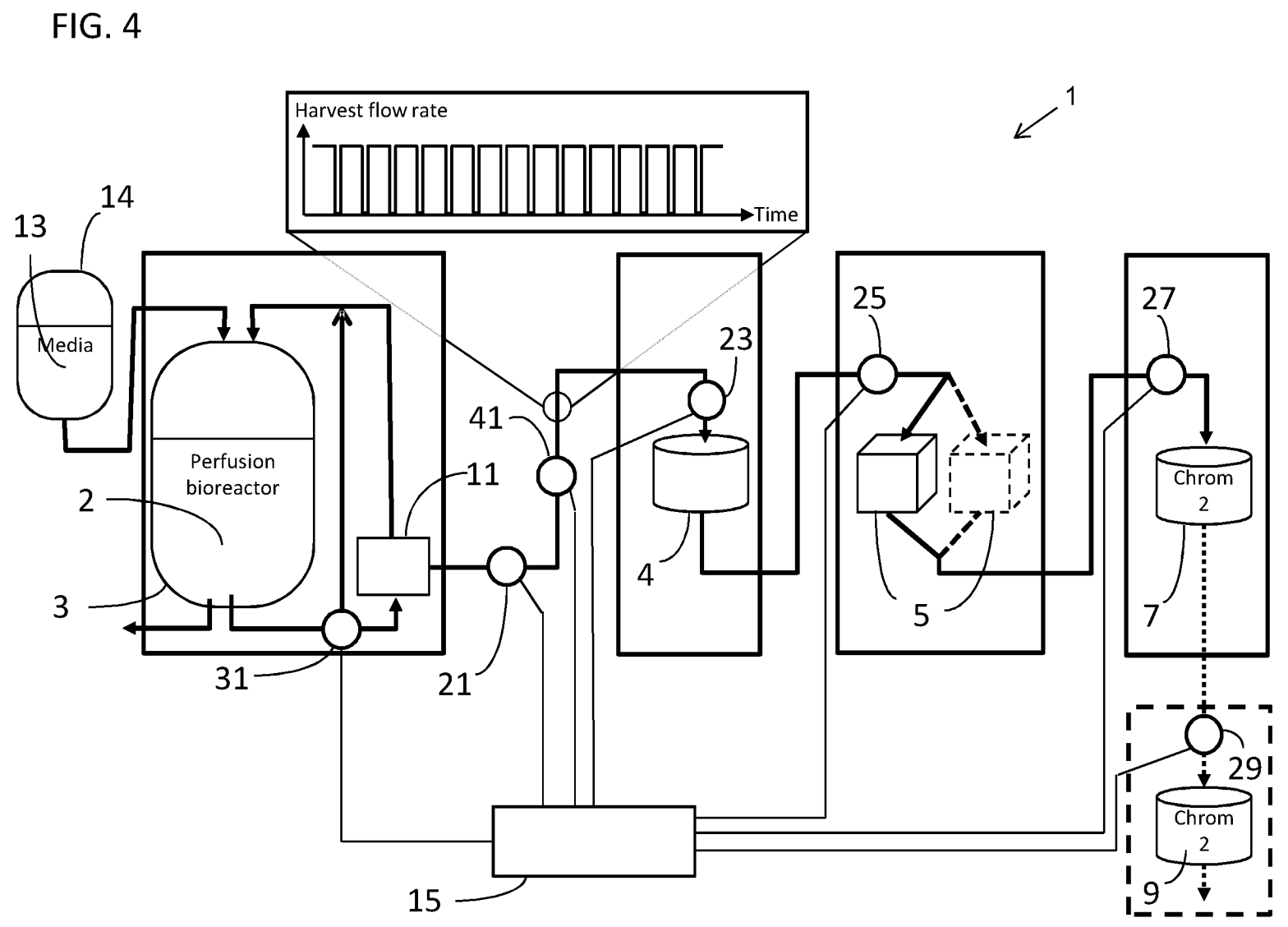
Figure 6:
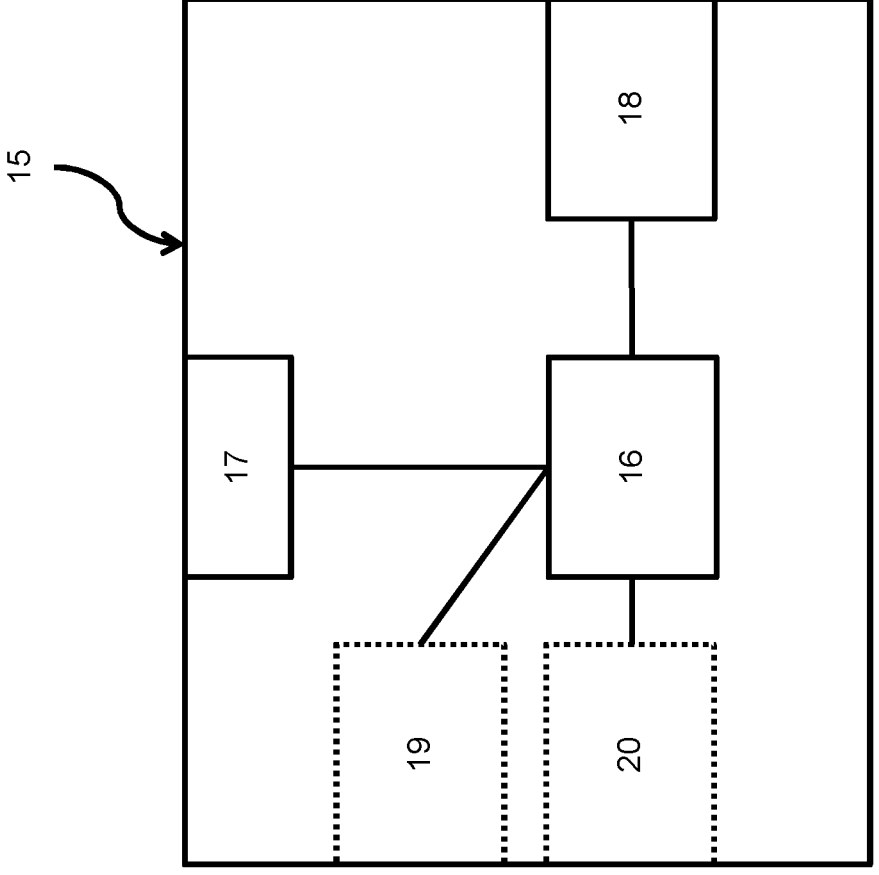
FIG. 6 shows the controller according to one or more embodiments of the present disclosure.

FIG. 4 shows a bioprocessing system 1 comprising all the components already described in relation to FIG. 2 (see above) and further including a controller 15, further described in relation to FIG. 6, which system may be used to perform the method 600 according to one or more embodiments of the present disclosure. The bioprocessing system 1 shown in FIG. 4 further comprises at least one sensor 41 configured to perform a chemical and/or biochemical analysis of a fluid 2, and/or configured to measure a time period, and provide measurement results comprised in a control signal. It is to be understood that a chemical or biochemical analysis of the fluid 2 may be performed before or after any processing step of the method according to the present disclosure, i.e. before or after forwarding of the fluid 2 to any device or unit of the bioprocessing system 1. Alternatively and/or additionally, measurement of a time period may be performed during any processing step of the method according to the present disclosure. Consequently, the at least one sensor 41 may be configured to be comprised in any component of the bioprocessing system 1 or configured to be inserted into any component of the bioprocessing system 1 such that the at least one sensor 41 is at least in part in contact with the fluid 2 to be analysed. Components of the bioprocessing system 1 include, but are not limited to, the perfusion bioreactor 3, the cell retention device 11, the first separation device 4, the virus inactivation vessel(s) 5, the second separation device 7, the third separation device 9, and flow channels connecting any two of the above-mentioned components and transporting the fluid 2 between any of the above-mentioned components. The skilled person will readily understand that the at least one sensor 41 may alternatively and/or additionally be located separately from the bioprocessing system 1, meaning that a fluid 2 to be analysed must be sampled and transferred from the system to the sensor 41 before analysis can be performed.

A chemical and/or biochemical analysis may be performed on the product fluid forwarded from the perfusion bioreactor before the product fluid enters the cell-retention device, before the product fluid is loaded on the first separation device, before the product fluid is filled in the virus inactivation vessel, before the product fluid is loaded on the second separation device, before the product fluid is loaded on the third separation device, and/or after the product fluid exits the third separation device. Non-limiting examples of chemical analysis which may be performed are spectrophotometry, and spectrometry. The at least one sensor 41 may in such cases e.g. be a probe designed to be in direct contact with the fluid and/or configured to generate an absorbance spectrum in the NIR wave length region. Alternatively or additionally the probe may e.g. be a probe designed to be in direct contact with the fluid and/or configured to generate a Raman spectrum, e.g. a spectrophotometry sensor, as commercially available from Hellma. Non-limiting examples of biochemical analysis which may be performed are different types of immunological assays or other protein binding assays, such as an enzyme-linked immunosorbent assay (ELISA). The at least one sensor 41 may in such cases e.g. be a probe designed to be in direct contact with the fluid and/or configured to generate a detectable signal by use of an enzyme when an immunological reaction takes place, for example binding of an antibody or antibody fragment to an antigen, wherein the antibody or antibody fragment has been produced by the biological cells in the perfusion bioreactor. Another non-limiting example of a biochemical analysis which may be performed is a fluorescence-based assay (including fluorescence immunoassays, protein binding assays, and other saturation assay techniques, as well as bioassay techniques), in which case the sensor 41 may e.g. be a probe designed to be in direct contact with the fluid and/or configured to generate a detectable signal by use of a fluorescent label. Alternatively or additionally, a flow injection analysis may be performed on the fluid, in which case at least one sensor 41 may be a flow injection analysis sensor. Alternatively or additionally, the at least one sensor 41 may be a probe designed not to be in direct contact with the fluid and/or configured to generate a signal based on an off-line analysis such as affinity based product titer determination or surface plasmon resonance. Further non-limiting examples of chemical or biochemical analysis that may be performed on the fluid are analyses of pH, conductivity, aggregate formation (e.g. by use of a light scattering sensor, such as Viscotek TDAmax system from Malvern Instruments), and/or purity of product output by use of high performance liquid chromatography (HPLC) and/or mass spectrometry.

Non-limiting examples of time periods which may be measured for the purpose of obtaining measurement results and generating control parameters are the time period of at least a part of a bioreactor cycle, such as the bioreactor product output time period and/or the bioreactor non-product output time period, and/or the time period of at least a part of a first separation cycle, such as the first separation loading time period, the first separation wash time period, the first separation product elution time period, and/or the first separation regeneration time period, and/or the time period of at least a part of a second separation cycle, such as the second separation loading time period, the second separation wash time period, the second separation product elution time period, and/or the second separation regeneration time period, and/or the time period of at least a part of a third separation cycle, such as the third separation loading time period, the third separation wash time period, the third separation product elution time period, and/or the third separation regeneration time period, and/or the time period of at least a part of a virus inactivation cycle, such as the virus inactivation fill time period, the virus inactivation pH decrease time period, the virus inactivation decreased pH hold time period, the virus inactivation pH increase and buffer adjustment time period, the virus inactivation product output time period, and/or the virus inactivation regeneration time period. Currently preferred time periods to measure are one or more separation loading time periods, one or more separation elution time periods, the virus inactivation decreased pH hold time period, the virus inactivation pH increase and buffer adjustment time period, and/or the virus inactivation product output time period. It is to be understood that it is possible to measure different time periods during different cycles, and further that some time periods are not necessary to measure in each cycle, in particular the bioreactor time periods in embodiments where the bioreactor is in a quasi-steady state.

The controller 15 is communicatively coupled to the at least one sensor 41, the first controllable forwarding unit 21, the first controllable loading unit 23, the second controllable loading/filling unit 25, the third controllable loading unit 27 and the fourth controllable loading unit 29. The controller is further configured to receive/send control signals to/from the at least one sensor 41, the first controllable forwarding unit 21, the first controllable loading unit 23, the second controllable loading/filling unit 25, the third controllable loading unit 27 and the fourth controllable loading unit 29. Likewise, the controller 15 is communicatively coupled to any further controllable forwarding unit, controllable loading unit, and/or controllable flow unit. The controller is further configured to receive/send control signals to/from any such further controllable forwarding unit, controllable loading unit, and/or controllable flow unit.

In one example, the controller 15 comprises a model or a plurality of models, used to generate and/or predict values of bioprocessing properties/bioprocessing variables. The most important input parameters to the model(s) are the flow rate of medium into the bioreactor and the product titer (i.e. the concentration or amount of target biomolecule) in the harvest (i.e. in the product fluid) at different stages of the process. Based on these input parameters, the different times and flow rates in the model(s) can be determined. Another input parameter may be the amount or concentration of impurities in the product fluid at different stages in the process. The controller 15 obtains/receives measurement results in a control signal from the at least one sensor 41, e.g. a NIR spectrum/spectra. The measurement results are obtained by the sensor 41 by performing spectrophotometry of the fluid 2 forwarded from the bioreactor 3 in the bioprocessing system 1. The controller 15 then puts the measurement results into the model(s) to generate/predict control parameters based on the measurement results and the model(s). The generated control parameters may e.g. define how much the flow of the product fluid should be adapted in response to the measurement results. The controller 15 may further be configured to control the bioprocess using the generated parameters.

Figure 5:
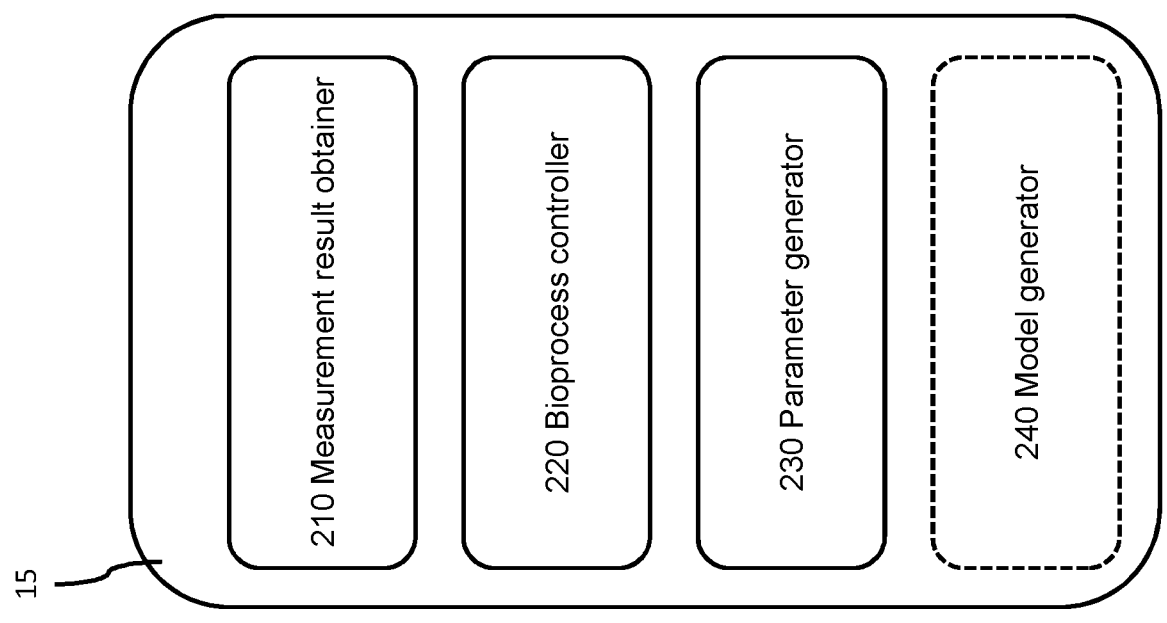
FIG. 5 illustrates functional modules of the controller according to one or more embodiments of the present disclosure.

FIG. 5 illustrates functional modules of the controller 15 according to one or more embodiments of the present disclosure. It is appreciated that the functionality of the controller 15 may be distributed over fewer or further functional modules depending on the application, and that the purpose of the concept of functional modules is used for illustrative purposes. In other words, the functionality of the controller may be concentrated to a single functional module or distributed over a plurality of functional modules without departing from the scope of the present disclosure.

In one embodiment, the controller 15 comprises a measurement result obtainer module 210. The measurement result obtainer module 210 is primarily configured to obtain measurement results by performing a chemical or biochemical analysis of the fluid 2 and/or by measuring a time period of performing at least a part of a method for separating a biomolecule. The measurement results are typically obtained by receiving a control signal from the at least one sensor 41. The control signal typically comprises an indication of the measurement results resulting from performing chemical or biochemical analysis of the fluid 2, such as from performing spectrophotometry of the fluid 2, e.g. indicative of quantitative measurements of the reflection or transmission properties of the fluid 2 as a function of wavelength of emitted light by the sensor 41.

In one example, the measurement result comprises a generated spectrum of the bioprocess fluid, the spectrum showing the specific reflection/absorbance values of spectrum of light, e.g. a Near Infra-Red, NIR. In other words, reflection/absorbance values as a function of the wavelength of the emitted light. The reflection/absorbance values at specific wavelengths can be related to the molecular structures present in the bioprocess fluid and is accordingly indicative of the chemical composition of the fluid. The spectrum resulting from a full NIR scan may include a wavelength range between 800-2500 nm. If the wanted variable includes content of a protein, the spectrum resulting from a NIR scan may preferably include a wavelength range between 1100 nm and 2500 nm. If the wanted variable includes content of a carbohydrate, the spectrum resulting from a NIR scan may preferably include a wavelength range of 1740-1800, 2100-2300 and/or 2410-2490 nm.

In one embodiment, the controller 15 comprises a bioprocess controller module 220. The bioprocess controller module 220 is typically configured to control a flow of product fluid from the bioreactor 3, and/or to control the length of the bioreactor product output time period and/or the bioreactor non-product output time period. The flow is typically controlled in response to values of wanted variables generated or predicted by the one or more models.

In one example, the controller 15 controls the flow of product fluid from the bioreactor 3 by sending a control signal to the first controllable forwarding unit 21. The first controllable forwarding unit 21 typically comprises a valve unit and the control signal activates or controls one or more valves of the valve unit. E.g. the flow of product fluid is controlled to a certain volume per time unit.

In one example, the controller 15 controls the flow of product fluid to the first separation device 4 by sending a control signal to the first controllable loading unit 23. The first controllable loading unit 23 typically comprises a pump and the flow of the pump is controlled by the control signal. E.g. the flow of product fluid into the first separation device 4 is controlled to a certain volume per time unit.

In one embodiment, the controller 15 comprises a parameter generator module 230. The parameter generator module 230 is typically configured to generate control parameters based on the measurement results of the at least one sensor 41 and/or the one or more models. The control parameters typically reflect the responsiveness, of the bioprocess controller module 220 and/or one or more PID controllers external to the controller 15 controlling the flow of product fluid from the bioreactor 3 and/or or the flow of product fluid to the first separation device 4, to changes in measurement result values, e.g. a decreased content of target biomolecule in the fluid 2 or density of viable cells in the fluid 2.

In one example, a change in reflection or transmission properties of the fluid 2 indicated by the measurement results may indicate that there has been a change (increase or decrease) in the product titer, or a change (increase or decrease) in the amount or concentration of host cell proteins (HCP) The parameter generator module 230 may then generate control parameters e.g. indicating that cycle times should be adjusted.

In one embodiment, the controller 15 comprises an optional model generator module 240. The model generator module 240 may generate the one or more models by performing orthogonal partial least squares analysis using a reference data set and/or a starting data set to, as further described in relation to FIG. 4, determine correlations between the wanted variables and extended reference measurement results, e.g. comprised in the reference data set and/or a starting data set, for a reference set of bioprocessing conditions.

A reference data set and/or a starting data set may be generated by proven methods in order to determine the reference value for various process parameters at various time points of the process. The proven methods may involve measuring reflection and/or transmission properties of the fluid 2 as reference measurement results and simultaneously determining values of wanted variables of the bioprocess as reference predicted variables, e.g. determining a target biomolecule content of the fluid 2. Parameters of particular interest for the model are considered as wanted parameters or parameters of interest to determine and/or control, but also parameters that might influence the spectrum recorded without being of interest to determine or control. For example, known data regarding the host cell line and the starting process parameters may be a suitable starting data set, and as the process proceeds the reference values for various process parameters are updated and/or adapted based on the measurements performed, e.g. by the at least one sensor 41. Existing knowledge of cell specific productivities and cell specific perfusion rates, may be used to obtain a good estimate of product titers, required media flow rates etc. An example of conventional methods performing multivariate data analysis, MVDA, employing unsupervised principal component analysis, PCA, and partial least squares regression methods, PLS, for prediction of multiple cultivation variables during bioprocess-monitoring can be found in "Chemometrics and in-line near infrared spectroscopic monitoring of a biopharmaceutical Chinese hamster ovary cell culture: prediction of multiple cultivation variables", Clavaud M, Roggo Y, Von Daeniken R, Liebler A, Schwabe J O, Talanta 26 Mar. 2013, 111:28-38.

The reference data set can then be transformed into a computer model by means of analyzing the absorbance as a function of wavelength and corresponding determined parameter values, e.g. indicative of process time point, and relating this absorbance to the parameter values determined by the proven methods. An example on how variables can be predicted using a model generated based on reference data can be found in "Designing a calibration set in spectral space for efficient development of an NIR method for tablet analysis", M Anik Alama, James Drennen III, Carl Anderson, Journal of Pharmaceutical and Biomedical Analysis Volume 145, 25 Oct. 2017, Pages 230-239.

According to a third aspect, as illustrated in FIG. 6, the present disclosure provides a controller 15, which comprises processing circuitry 16, and a memory 17, said memory 17 containing instructions executable by said processing circuitry 16, whereby said controller 15 is operative to perform any one or more of the steps of the above-described methods 100 and 600, respectively. The memory 17 may alternatively be called a transitory medium 17. The controller 15 may be in the form of e.g. an electronic control unit, a server, an on-board control unit, a stationary computing device, a laptop control unit, a tablet control unit, a handheld control unit, a wrist-worn control unit, a smart watch, a smartphone or a smart TV. The controller 15 may comprise processing circuitry 16 communicatively coupled to a communications interface, e.g. a transceiver 18, configured for wired or wireless communication. The controller 15 may further comprise at least one optional antenna (not shown in figure). The antenna may be coupled to the transceiver 18 and is configured to transmit and/or emit and/or receive wired or wireless signals in a communication network, such as WiFi, Bluetooth, 3G, 4G, and 5G etc. In one example, the processing circuitry 16 may be any of a selection of a processor and/or a central processing unit and/or processor modules and/or multiple processors configured to cooperate with each-other. Further, the controller 15 may comprise a memory 17 communicatively coupled to the processing circuitry 16. The memory 17 may e.g. comprise a selection of a hard RAM, disk drive, a floppy disk drive, a flash drive or other removable or fixed media drive (non-transitory medium) or any other suitable memory known in the art. The memory 17 may contain instructions executable by the processing circuitry 16 to perform any of the steps or methods described herein. The processing circuitry 16 may be communicatively coupled to a selection of any of the transceiver 18 and the memory 17. The controller 15 may be configured to send/receive control signals directly to/from any of the above mentioned units or to external nodes or to send/receive control signals via a wired and/or wireless communications network.

The wired/wireless transceiver 18 and/or a wired/wireless communications interface may be configured to send and/or receive data values or parameters as a signal to or from the processing circuitry 16 to or from other external nodes.

In an embodiment, the transceiver 18 communicates directly to external nodes/units or via the wireless communications network. In one example, control parameters are sent to an external PID controller.

In one or more embodiments the controller 15 may further comprise an input device 20, configured to receive input or indications from a user and send a user input signal indicative of the user input or indications to the processing circuitry 16.

In one or more embodiments the controller 15 may further comprise a display 19 configured to receive a display signal indicative of rendered objects, such as text or graphical user input objects, from the processing circuitry 16 and to display the received signal as objects, such as text or graphical user input objects.

In one embodiment the display 19 is integrated with the user input device 20 and is configured to receive a display signal indicative of rendered objects, such as text or graphical user input objects, from the processing circuitry 16 and to display the received signal as objects, such as text or graphical user input objects, and/or configured to receive input or indications from a user and send a user-input signal indicative of the user input or indications to the processing circuitry 16.

In a further embodiment, the controller 15 may further comprise and/or be coupled to one or more additional sensors (not shown in the figure) configured to receive and/or obtain and/or measure physical properties pertaining to the bioprocessing system SYS and send one or more sensor signals indicative of the physical properties to the processing circuitry 16. An example of such an additional sensor may be an ambient air pressure sensor configured to measure the ambient air pressure where the bioprocessing system SYS is located.

In one or more embodiments, the processing circuitry 16 is further communicatively coupled to the input device 20 and/or the display 19 and/or the additional sensors.

In embodiments, the communications network communicate using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the control unit CU may comprise the necessary communication capabilities in the form of e.g., functions, means, units, elements, etc., for performing the present solution. Examples of other such means, units, elements and functions are: processors, memory, buffers, control logic, encoders, decoders mapping units, multipliers, decision units, selecting units, switches, modulators, demodulators, inputs, outputs, antennas, amplifiers, receiver units, transmitter units, DSPs, power supply units, power feeders, communication interfaces, communication protocols, etc. which are suitably arranged together for performing the present solution.

Especially, the processing circuitry of the present disclosure may comprise one or more instances of a processor, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

Further, according to a fourth aspect the present disclosure provides a computer program comprising computer-executable instructions for causing a controller 15, when the computer-executable instructions are executed on processing circuitry 16 comprised in the controller 15, to perform any one or more of the steps of the above-described methods 100 and 600, respectively.

According to a fifth aspect, the present disclosure provides a computer program product comprising a computer-readable storage medium, the computer-readable storage medium having the computer program as described above embodied therein.

Devices "comprising" one or more recited elements may also include other elements not specifically recited. The term "comprising" includes as a subset "consisting essentially of" which means that the device has the components listed without other features or components being present. Likewise, methods "comprising one or more recited steps may also include other steps not specifically recited.

The singular "a" and "an" shall be construed as including also the plural.

EXAMPLES

Example 1

The typical length of a perfusion process run of around one month is a good match with the typical lifetime of a constantly cycled chromatography column run in batch mode. According to a non-limiting example, assuming that the chromatography resin lasts for 100 cycles and the perfusion process runs for 25 days, the flow rates of the chromatography step may be designed to make the chromatography step last 6 hours per cycle, i.e. 4 cycles per 24 hours, and 100 cycles during the perfusion run. This enables the resin lifetime to be fully utilized, while removing the needs to replace column during the perfusion run or to store the column after the run. Hereby, true single-use resin chromatography is enabled in a cost-effective way. The 6 hours per cycle may for example be divided into 4 hours of loading of the chromatography column and 2 hours of wash, elution and regeneration of the chromatography column. If, in this example, the reactor volume per day (RV/day) is set to 1 in the perfusion process, the flow rate out of the perfusion bioreactor should be set to 0.0625 RV/h during the 4 hours of loading of the chromatography column, and the flow rate out of the perfusion bioreactor should be set to 0 RV/h during the 2 hours of wash, elution and regeneration of the chromatography column.

Example 2

Figure 7:
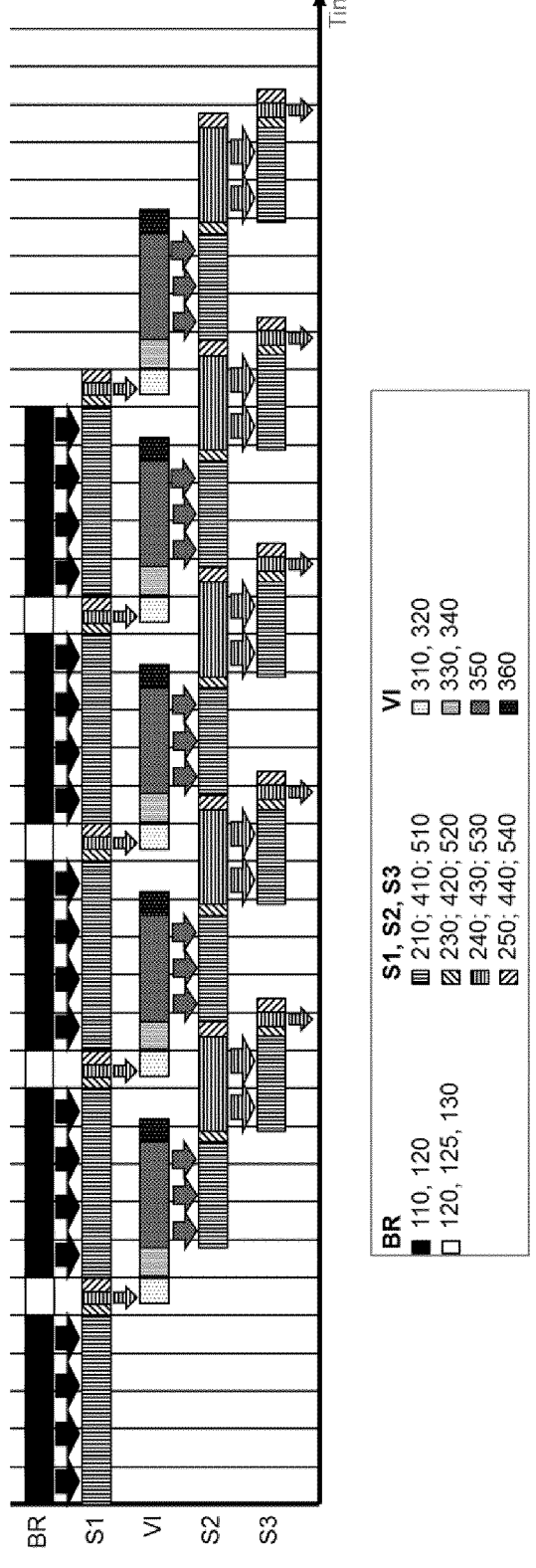
FIG. 7 is a schematic process timing chart of a non-limiting embodiment of the presently disclosed method, including a 3-step chromatography, wherein each chromatography step is a bind/elute process.

In a non-limiting embodiment, the presently disclosed method comprises three separation steps wherein each separation step is a chromatography process, wherein each chromatography step is a bind/elute process, as shown in the schematic process timing chart of FIG. 7.

Example 3

Figure 8:
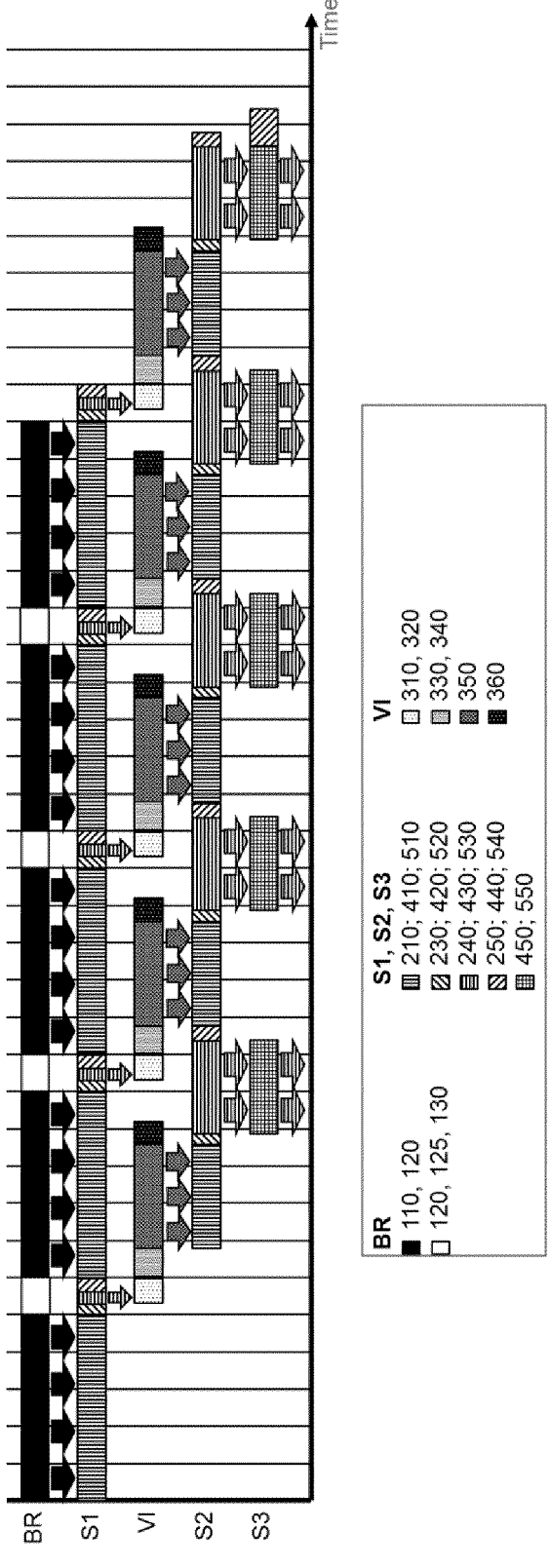
FIG. 8 is a schematic process timing chart of a non-limiting embodiment of the presently disclosed method, including a 3-step chromatography, wherein the first and second chromatography steps are bind/elute processes and the third chromatography step is a flow-through process.

According to another non-limiting embodiment, the presently disclosed method comprises three separation steps wherein each separation step is a chromatography process, wherein the first and second chromatography steps are bind/elute processes and the third chromatography step is a flow-through process, as shown in the schematic process timing chart of FIG. 8.

Example 4

Figure 9:
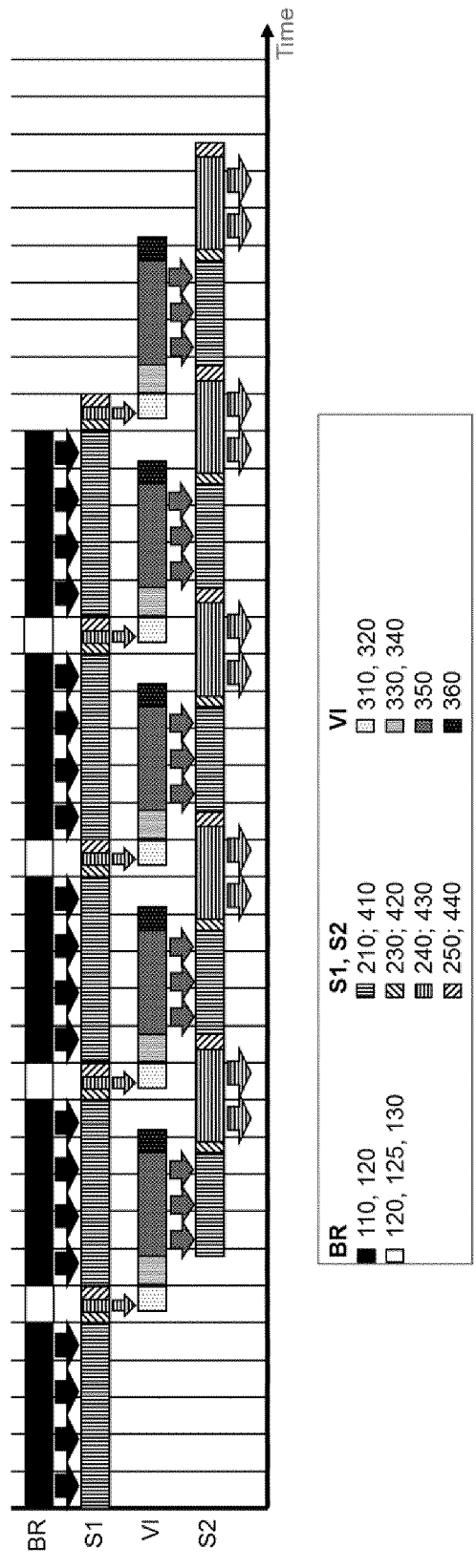
FIG. 9 is a schematic process timing chart of a non-limiting embodiment of the presently disclosed method, including a 2-step chromatography, wherein each chromatography step is a bind/elute process.

In a further non-limiting embodiment, the presently disclosed method comprises two separation steps wherein each separation step is a chromatography process, wherein each chromatography step is a bind/elute process, as shown in the schematic process timing chart of FIG. 9.

Example 5

Figure 10:
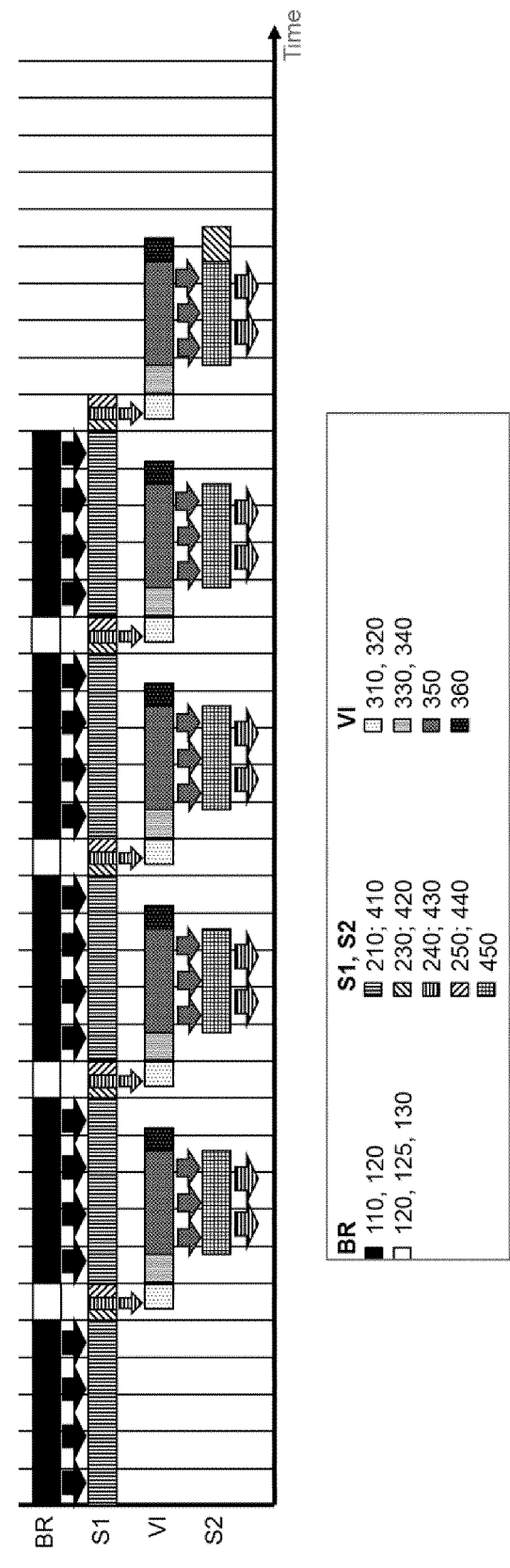
FIG. 10 is a schematic process timing chart of a non-limiting embodiment of the presently disclosed method, including a 2-step chromatography, wherein the first chromatography step is a bind/elute process and the second chromatography step is a flow-through process.

According to yet another non-limiting embodiment, the presently disclosed method comprises two separation steps wherein each separation step is a chromatography process, wherein the first chromatography step is a bind/elute process and the second chromatography step is a flow-through process, as shown in the schematic process timing chart of FIG. 10.

Example 6

According to yet another non-limiting embodiment, of which a specific example is described below, the presently claimed method was carried out as follows.

A mAb producing CHO-K1 Chinese Hamster Ovary cell line was cultivated in a ReadyToProcess WAVE25 bioreactor (GE Healthcare Life Sciences, Sweden). The cultivation was performed using 2 L perfusion Cellbag with 500 mL working volume (CB0002L10-04, GE Healthcare Life Sciences, Sweden). The Cellbag included an integrated perfusion filter with a pore size of 7 μm. The cells were inoculated from a shake flask culture at around 10×106 cells/mL into the bioreactor and were grown in chemically defined HyClone™ ActiPro medium (GE Healthcare Life Sciences, Sweden). The temperature was set to 37° C., and the pH was maintained at 6.9 by addition of $CO_2$ into the headspace of the bioreactor and 8% sodium bicarbonate. The dissolved oxygen concentration (DO) was kept at 40% by enriching the headspace air with oxygen and by adapting the rocking rate.

The feed medium consisted of a mixture of HyClone ActiPro medium, HyClone Cell Boost 1 and Cell Boost 3 (GE Healthcare Life Sciences, Sweden) in a volumetric ratio of 1:0.139:0.158.

The harvest was performed intermittently with a pump through the perfusion filter, i.e. harvest was only removed when the capture chromatography system was loading the Protein A column. The rhythm for harvest was 6 hours on, which corresponds to the load cycle, and 2 hours off to accommodate the wash, elution, strip flush, CIP and re-equilibration cycles. The perfusion feed rate was varied during this 8-hour cycles to maintain a constant weight of 0.5 kg.

The harvest was transferred through a 0.2 μm filter (ULTA Prime CG 2-inch capsule, GE Healthcare) to a hold-up flask prior to loading on the chromatography system. To monitor and prevent blockage of the clearing filter a pressure sensor was installed upstream of the clearing filter. The hold-up flask was a sterile 200 mL glass bottle with three ports for harvest inlet, harvest outlet and a 0.2 μm air filter. It was placed on a second wave platform to continuously monitor the weight and synchronous operation of harvest flow from the bioreactor to the Äkta system. The perfusion, i.e., addition of feed medium and harvest removal, was initiated immediately after the inoculation. The cells were grown to a target cell density of 45×106 cells/mL with a stepwise increase of the perfusion rate before cell bleeding was applied to keep the cell density constant. Bleeding was done continuously, based on an estimated growth rate. At steady state, a cell specific perfusion rate (CSPR, given as the perfusion rate divided by the cell density) of 30 pL/cell/day was applied.

An Äkta Pure chromatography system was aseptically connected to the hold-up flask and equipped with two 1 mL HiTrap PrismA columns (GE Healthcare). After isocratic elution, the product was processed in a virus inactivation step at pH 3.5 for 60 minutes.

All process steps from perfusion to virus inactivation were performed in a closed flow path.

Figure 11:
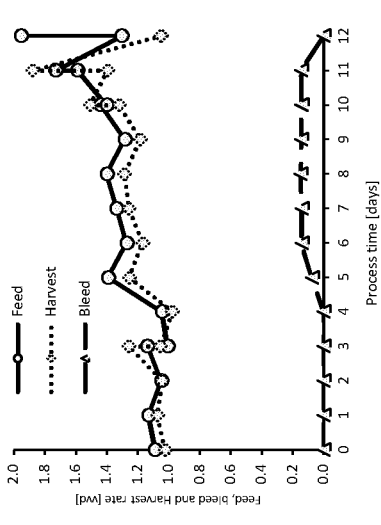
FIG. 11 illustrates the growth performance of the WAVE25 bioreactor, including perfusion culture data showing VCD and viability (A.), CSPR (B.), feed-, bleed- and harvest rates (C.), growth rate (D.) and product titers (E.)
Figure 11:
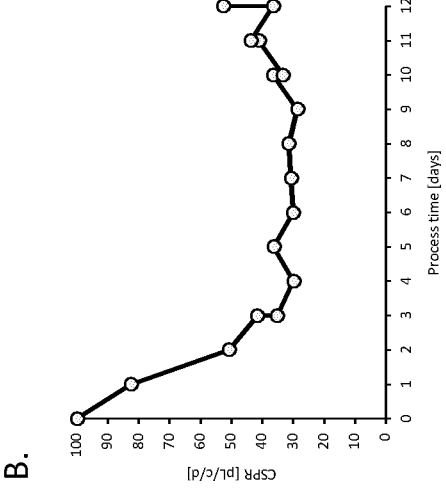
Figure 11:
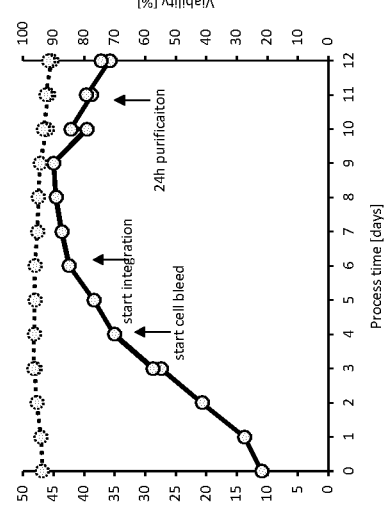
Figure 11:
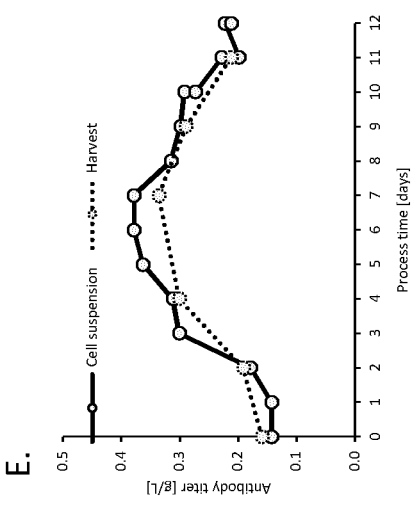
Figure 11:
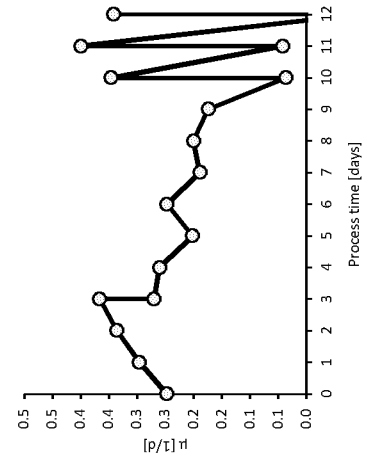

The Growth performance of the WAVE25 bioreactor is shown in FIG. 11. The culture reached a steady state of about 45×10⁶ cells/mL at day eight. The intermittent harvest removal was started the same day. Other culture parameters shown are the CSPR, feed, bleed and harvest rates, growth rate and product titers. In summary, the perfusion process delivered a representative harvest to be processed in the connected downstream process. Specifically, FIG. 11 provides perfusion culture data showing VCD and viability (A.), CSPR (B.), feed-, bleed- and harvest rates (C.), growth rate (D.) and product titers (E.) for the twelve-day process operated in intermittent harvest mode. Cell bleeding was initiated on day four to reach a final peak viable cell density of 45×106 cells/mL with a titer of 0.3 g/L on day eight, when the downstream process integration was started followed by a completely automatic purification cycle for 24 hours on day eleven. No sieving effect was observed indicated by similar titer of the cell suspension and harvest (E.).

Starting on Day 8, the intermittently removed harvest was applied on the capture step. The harvest flow was controlled by the load pump of the Äkta Pure system, minimizing the hold-up volume in the surge flask to below 50 mL.

Figure 12:
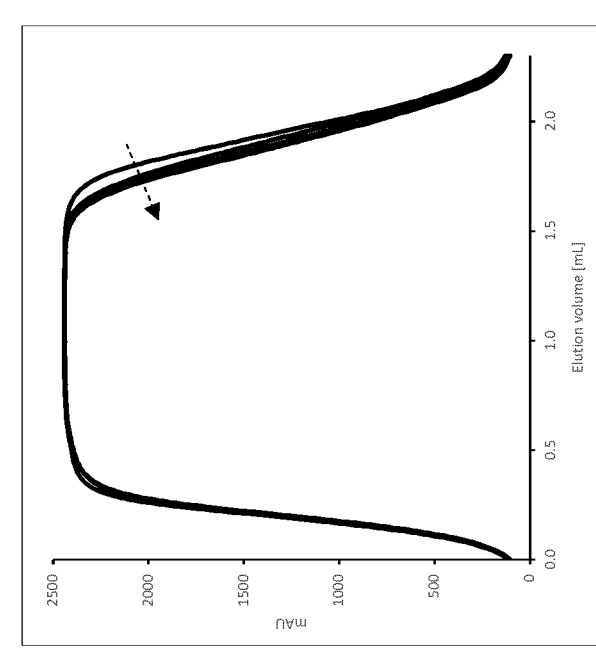
FIG. 12 illustrates elution peaks from four subsequent capture steps of the integrated fully-automated cycle on day elven until day twelve (A.), and full UV-chromatogram of the protein A capture step (B.).

The connected set-up of the perfusion bioreactor and the capture step was operated for four days. Chromatograms from the four cycles on day eleven are shown in FIG. 12. Specifically, FIG. 12 illustrates elution peaks from four subsequent capture steps of the integrated fully-automated cycle on day elven until day twelve (A.). Full UV-chromatogram of the protein A capture step is also illustrated (B.). Overlay of the elution peaks show decrease of the peak width according to the decrease of harvest titer (arrow).

The yield in the capture step was tracked for some capture cycles. The amount of material found in the elution peak was proportional to the harvest titer and harvest volume, indicating a yield close to 100%. Furthermore, the shape of the elution peaks was analyzed and found to be consistent over the process of 4 days, also indicating consistent process quality.

Virus inactivation, i.e., low pH hold was performed batchwise for each eluate pool.

The above-descried example demonstrates that a continuous perfusion bioreactor can be connected to a single chromatography column by letting the chromatography loading cycle control the harvest flow rate. With this strategy, the volume in the bioreactor varied slightly, however, only a minimal surge vessel volume was needed.

It is to be understood that the present disclosure is not restricted to the above-described exemplifying embodiments thereof and that several conceivable modifications of the present disclosure are possible within the scope of the following claims.

The invention claimed is:

1. A method for separating a biomolecule from a fluid, wherein the biomolecule is produced by biological cells in a perfusion bioreactor provided as part of a bioprocessing system not having a surge tank after the bioreactor, the method comprising:

110. forwarding a product fluid comprising the biomolecule and biological cells from the perfusion bioreactor during a bioreactor product output time period, $t_{BRp}$, which constitutes a first part of a bioreactor cycle time period, $t_{BR}$;

210. loading a first separation device with the product fluid obtained in step 110 during a first separation loading time period, $t_{S1l}$, which constitutes a first part of a first separation cycle time period $t_{S1}$;

130. pausing the forwarding of the product fluid from the perfusion bioreactor during a bioreactor non-product output time period, $t_{BRn}$, which constitutes a second part of the bioreactor cycle time period; and 220. pausing the loading of the first separation device during a second part of the first separation cycle time period, said second part comprising:

optionally a first separation wash time period, $t_{S1w}$, a first separation product elution time period, $t_{S1p}$, and a first separation regeneration time period, $t_{S1r}$;

wherein $$t_{BR}=t_{BRp}+t_{BRn},$$

$$t_{S1}>=t_{S1l}+t_{S1w}+t_{S1p}+t_{S1r},$$

and $$t_{BRn}>=t_{S1w}+t_{S1p}+t_{S1r};$$

repeating steps 110, 210, 130, and 220 n times, wherein n is the number of times required to complete a production run.

2. The method according to claim 1, wherein the forwarding of the product fluid from the perfusion bioreactor and the loading of the first separation device with the product fluid are performed substantially simultaneously.

3. The method according to claim 1, wherein the second part of the first separation cycle time period comprises:

optionally causing a washing liquid to pass through the first separation device during the optional first separation wash time period, forwarding a product fluid from the first separation device during the first separation product elution time period, and regenerating the first separation device during the first separation regeneration time period.

4. The method according to claim 1, further comprising a virus inactivation cycle, performed during a virus inactivation cycle time period, $t_{V1}$, following the first separation cycle.

5. The method according to claim 1, wherein the virus inactivation cycle comprises:

filling a virus inactivation vessel during a virus inactivation fill time period, $t_{V1f}$, with the product fluid obtained from the first separation cycle.

6. The method according to claim 5, wherein the forwarding of the product fluid from the first separation device and the filling of the virus inactivation vessel with said product fluid are performed substantially simultaneously.

7. The method according to claim 5, wherein the virus inactivation cycle further comprises:

decreasing the pH during a virus inactivation pH decrease time period, $t_{V1d}$, holding the decreased pH during a virus inactivation decreased pH hold time period, $t_{V1h}$, increasing the pH and adjusting the buffer during a virus inactivation pH increase and buffer adjustment time period, $t_{V1i}$, forwarding a product fluid from the virus inactivation vessel during a virus inactivation product output time period $t_{V1p}$, and optionally regenerating the virus inactivation vessel during a virus inactivation regeneration time period $t_{V1r}$.

8. The method according to claim 7, wherein $$t_{V1}=t_{V1f}+t_{V1d}+t_{V1h}+t_{V1i}+t_{V1p}+\text{optionally }t_{V1r};\text{ and}$$

$$t_{BR}-t_{S1p}>=t_{V1d}+t_{V1h}+t_{V1i}+t_{V1p}+\text{optionally }t_{V1r}.$$

9. The method according to claim 7, wherein the filling comprises alternatingly filling two virus inactivation vessels during the virus inactivation fill time period, $t_{V1f}$, with the product fluid obtained from the first separation cycle;

wherein the forwarding of the product fluid from the first separation device and the alternating filling of the two virus inactivation vessels with said product fluid are performed substantially simultaneously;

$$t_{V1}=t_{V1f}+t_{V1d}+t_{V1h}+t_{V1i}+t_{V1p}+\text{optionally }t_{V1r};\text{ and}$$

$$2t_{BR}-t_{S1p}>=t_{V1d}+t_{V1h}+t_{V1i}+t_{V1p}+\text{optionally}$$
$$t_{V1r}>=t_{BR}-t_{S1p}.$$

10. The method according to claim 9, wherein the filling comprises alternatingly filling the two virus inactivation vessels during the virus inactivation fill time period with product fluid obtained from two or more of the first separation cycle.

11. The method according to claim 10, further comprising repeating the virus inactivation cycle n times or less.

12. The method according to claim 10, further comprising a second separation cycle, performed during a second separation cycle time period, $t_{S2}$, following the virus inactivation cycle, wherein $t_{BR}>=t_{S2}$.

13. The method according to claim 12, wherein the second separation cycle comprises:

loading a second separation device with the product fluid obtained from the virus inactivation cycle, during a second separation loading time period, $t_{S2l}$, which constitutes a first part of the second separation cycle time period, wherein the forwarding of the product fluid from the virus inactivation vessel and the loading of the second separation device with said product fluid are performed substantially simultaneously.

14. The method according to claim 12, wherein the second separation cycle, during a second part of the second separation cycle time period, comprises:

optionally causing a washing liquid to pass through the second separation device during a second separation wash time period, $t_{S2w}$, forwarding a product fluid from the second separation device during a second separation product elution time period, $t_{S2p}$, and regenerating the second separation device during a second separation regeneration time period, $t_{S2r}$;

wherein $t_{S2}>=t_{S2l}+t_{S2w}+t_{S2p}+t_{S2r}$.

15. The method according to claim 12, wherein the second separation cycle comprises:

causing the product fluid obtained from the virus inactivation cycle to flow through the second separation device during a second separation flow through time period, $t_{S2l}$, and regenerating the second separation device during a second separation regeneration time period, $t_{S2r}$;

wherein $t_{S2}>=t_{S2l}+t_{S2r}$, and wherein the forwarding of the product fluid from the virus inactivation vessel and the causing of said product fluid to flow through the second separation device are performed substantially simultaneously.

16. The method according to claim 12, further comprising repeating the second separation cycle n times.

17. The method according to claim 12, further comprising a third separation cycle, performed during a third separation cycle time period, $t_{S3}$, following the second separation cycle, wherein $t_{BR}>=t_{S3}$.

18. The method according to claim 17, wherein the third separation cycle comprises loading a third separation device with a product fluid obtained from the second separation cycle, during a third separation loading time period, $t_{S3l}$, which constitutes a first part of the third separation cycle time period $t_{S3}$, wherein the forwarding of said product fluid from, or the causing of said product fluid to flow through the second separation device, and the loading of the third separation device with said product fluid are performed substantially simultaneously.

19. The method according to claim 17, wherein a second part of the third separation cycle time period comprises:

optionally causing a washing liquid to pass through the third separation device during a third separation wash time period, $t_{S3w}$, forwarding a product fluid from the third separation device during a third separation product elution time period, $t_{S3p}$, and regenerating the third separation device during a third separation regeneration time period, $t_{S3r}$;

wherein $t_{S3}>=t_{S3l}+t_{S3w}+t_{S3p}+t_{S3r}$.

20. The method according to claim 17, wherein the third separation cycle comprises:

causing a product fluid obtained from the second separation cycle to flow through the third separation device during a third separation flow through time period, $t_{S3l}$, and regenerating the third separation device during a third separation regeneration time period, $t_{S3r}$;

wherein $t_{S3}>=t_{S3l}+t_{S3r}$, and wherein the forwarding of said product fluid from, or the causing of said product fluid to flow through, the second separation device and the causing of said product fluid to flow through the third separation device are performed substantially simultaneously.

* * * * *